US006495522B1

(12) United States Patent
Wang et al.

(10) Patent No.: US 6,495,522 B1
(45) Date of Patent: Dec. 17, 2002

(54) SUBSTITUTED ALPHA-HYDROXY ACID CASPASE INHIBITORS AND THE USE THEREOF

(75) Inventors: Yan Wang, San Diego, CA (US); Sui Xiong Cai, San Diego, CA (US); Eckard Weber, San Diego, CA (US); Gordon B. Mills, Houston, TX (US); Douglas R. Green, San Diego, CA (US); Lufeng Guan, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 55 days.

(21) Appl. No.: 09/649,810

(22) Filed: Aug. 28, 2000

Related U.S. Application Data

(60) Provisional application No. 60/151,077, filed on Aug. 27, 1999, and provisional application No. 60/158,373, filed on Oct. 12, 1999.

(51) Int. Cl.[7] ................... A61K 31/195; C07C 271/12; C07C 271/22; C07C 271/28
(52) U.S. Cl. ............... 514/19; 435/1.1; 435/2; 435/260; 435/405; 504/115; 514/183; 514/399; 514/478; 514/534; 514/538; 514/563; 558/275; 558/276; 560/37; 560/51; 560/129; 560/169; 560/170; 562/442; 562/553; 562/561; 562/569; 548/334.1
(58) Field of Search ............... 427/4; 435/1.1, 435/1.2, 1.3, 2, 260, 405; 504/115, 279, 303, 306, 317, 319, 320, 322; 514/19, 183, 399, 478, 534, 538, 563; 548/334.1; 558/275, 276; 560/37, 51, 129, 169, 170; 562/442, 553, 561, 567

(56) References Cited

U.S. PATENT DOCUMENTS

| | | | |
|---|---|---|---|
| 4,153,688 A | 5/1979 | Domicoli et al. ............ 424/177 |
| 4,518,528 A | 5/1985 | Rasnick .................... 260/112.5 |
| 5,221,607 A | 6/1993 | Cordell et al. ................. 435/6 |
| 5,252,463 A | 10/1993 | Nelson et al. ................ 435/23 |
| 5,416,013 A | 5/1995 | Black et al. ................ 435/226 |
| 5,430,128 A | 7/1995 | Chapman et al. ........... 530/330 |
| 5,434,248 A | 7/1995 | Chapman et al. ........... 530/330 |
| 5,462,939 A | 10/1995 | Dolle et al. .............. 514/231.5 |
| 5,585,357 A | 12/1996 | Dolle et al. .................... 514/18 |
| 5,624,672 A | 4/1997 | Bathurst et al. ......... 424/195.1 |
| 5,635,186 A | 6/1997 | Bathurst et al. ......... 424/195.1 |
| 5,635,187 A | 6/1997 | Bathurst et al. ......... 424/195.1 |
| 5,677,283 A | 10/1997 | Dolle et al. .................... 514/18 |
| 5,756,465 A | 5/1998 | Sleath et al. .................. 514/17 |
| 5,843,904 A | 12/1998 | Bemis et al. .................. 514/18 |
| 5,866,545 A | 2/1999 | Hagmann et al. ............. 514/18 |
| 5,869,519 A | 2/1999 | Karanewsky et al. ....... 514/415 |
| 5,871,724 A | 2/1999 | Iwata et al. ................ 424/85.1 |
| 5,877,197 A | 3/1999 | Karanewsky et al. ....... 514/397 |
| 5,932,549 A | 8/1999 | Allen et al. .................... 514/18 |
| 6,136,787 A | 10/2000 | Black et al. .................. 514/18 |
| 6,153,591 A | 11/2000 | Cai et al. ...................... 514/19 |
| 6,184,210 B1 | 2/2001 | Keana et al. .................. 514/19 |
| 6,184,244 B1 | 2/2001 | Karanewsky et al. ....... 514/419 |
| 6,200,969 B1 | 3/2001 | Fritz et al. ................... 514/214 |
| 6,201,118 B1 | 3/2001 | Robidoux et al. ........... 540/500 |
| 6,242,422 B1 | 6/2001 | Karanewsky et al. ......... 514/19 |
| 6,355,618 B1 | 3/2002 | Cai et al. ....................... 514/19 |

FOREIGN PATENT DOCUMENTS

| | | |
|---|---|---|
| EP | 0 519 748 A2 | 12/1992 |
| EP | 0 618 223 A2 | 10/1994 |
| EP | 623592 | * 11/1994 |
| JP | 11-1491 | 1/1999 |
| JP | 11-180891 | 7/1999 |
| WO | WO 93/05071 | 3/1993 |
| WO | WO 96/03982 | 2/1996 |
| WO | WO 96/20721 | 7/1996 |
| WO | WO 98/10778 | 3/1998 |
| WO | WO 98/11109 | 3/1998 |
| WO | WO 98/41232 | 9/1998 |
| WO | WO 99/18781 | 4/1999 |
| WO | WO 99/47154 | 9/1999 |
| WO | WO 99/56765 | 11/1999 |
| WO | WO 00/01666 | 1/2000 |
| WO | WO 00/23421 | 4/2000 |
| WO | WO 00/32620 | 6/2000 |

(List continued on next page.)

OTHER PUBLICATIONS

Ausili–Céfaro, G. and Marmiroli, L., "Supportive Care in Radiotherapy: A Review," *Tumori* 84:107–111, Il Pensiero Scientifico Editore (Mar.–Apr. 1988).

(List continued on next page.)

*Primary Examiner*—Jeffrey E. Russel
(74) *Attorney, Agent, or Firm*—Sterne, Kessler, Goldstein & Fox P.L.L.C.

(57) ABSTRACT

The present invention is directed to novel substituted α-hydroxy acid thereof, represented by the general Formula I:

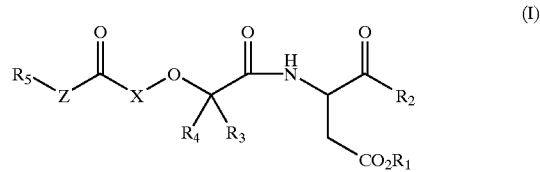

(I)

where $R_1$–$R_5$, X and Z are defined herein. The present invention also relates to the discovery that compounds having Formula I are potent inhibitors of caspases and apoptotic cell death. Therefore, the inhibitors of this invention can retard or block cell death in a variety of clinical conditions in which the loss of cells, tissues or entire organs occurs.

170 Claims, No Drawings

FOREIGN PATENT DOCUMENTS

| WO | WO 00/55114 A1 | 9/2000 |
|----|----------------|--------|
| WO | WO 00/55127 | 9/2000 |
| WO | WO 00/61542 A1 | 10/2000 |
| WO | WO 01/10383 A2 | 2/2001 |
| WO | WO 01/27140 A1 | 4/2001 |
| WO | WO 01/42216 A2 | 6/2001 |
| WO | WO 01/72707 | 10/2001 |
| WO | WO 01/90070 A2 | 11/2001 |
| WO | WO 01/94351 A1 | 12/2001 |

OTHER PUBLICATIONS

Braun, J.S. et al., "Neuroprotection by a caspase inhibitor in acute bacterial meningitis," Nat. Med. 5:298–302, Nature America Incorporated (Mar. 1999).

Chabrier, P.–E. et al., "BN 80933, a dual inhibitor of neuronal nitric oxide synthase and lipid peroxidation: A promising neuroprotective strategy," Proc. Natl. Acad. Sci. USA 96:10824–10829, The National Academy of Sciences (Sep. 1999).

Ezzell, C., "Alzheimer's Alchemy. Turning an innocuous nerve–cell protein into brain–wrecking beta amyloid," Sci. News 141:152–153, Science News (1992).

Loprinzi, C.L. et al., "Alleviation of Cytotoxic Therapy–Induced Normal Tissue Damage," Semin. Oncol. 22:95–97, W.B. Saunders Company (1995).

Morrison, R.T. and Boyd, R.N., "Organic Chemistry," Third Edition, Allyn and Bacon, Inc., Boston, MA, pp. 22 and 456 (1973).

Rapoport, A.P. et al., "Analysis of Factors That Correlate With Mucositis in Recipients of Autologous and Allogenic Stem–Cell Transplants," J. Clin. Oncol. 17:2446–2453, Lippincott Williams & Wilkins (Aug. 1999).

Schierle, G.S. et al., "Caspase inhibition reduces apoptosis and increases survival of nigral transplants," Nat. Med. 5:97–100, Nature Amerca Incorporated (Jan. 1999).

Varon, S. et al., "Neuronotrophic and Neurite–Promoting Factors and Their Clinical Potentials," Dev. Neurosci. 6:73–100, S. Karger Medical and Scientific Publishers (1983/84).

Co–pending U.S. patent application Ser. No. 09/987,417, Cai, S.X. et al., filed Nov. 14, 2001.

Dialog File 351, Accession No. 12319369, Derwent WPI English language abstract for JP 11–1491 (Jan. 6, 1999).

WPINDEX, Accession No. 1999–439401, Derwent WPI English language abstract for JP 11–180891 (Jul. 6, 1999).

Black, R.A. et al., A Pre–aspartate–specific Protease from Human Leukocytes That Cleaves Pro–interleukin–1β, J. Biol. Chem. 264:5323–5326, The American Society for Biochemistry and Molecular Biology, Baltimore, MD (1989).

Black, S.C. et al., "Co–localization of the Cysteine Protease Capspase–3 with Apoptotic Myocytes after In Vivo Myocardial Ischemia and Reperfusion in the Rat," J. Mol. Cell. Cardiol. 30:733–742, Academic Press, Inc., New York, NY (Apr. 1998).

Bourne, E.J. et al., "Studies of Trifluoroacetic Acid. Part XVIII. Reaction of N–Aroylglycines with Perfluoro–carboxylic Anhydrides." J. Chem. Soc. Part II:1771–1775, The Chemical Society, London, England (1961).

Alnemri, E.S. et al., "Human ICE/CED–3 Protease Nomenclature," Cell 87:171, Cell Press, Cambridge, MA (1996).

An, S. and Knox, K.A., "Ligation of CD40 rescues Ramos–Burkitt lymphoma B cells from calcium ionophore– and antigen receptor–triggered apoptosis by inhibiting activation of the cysteine protease CPP32/Yama and cleavage of its substrate PARP," FEBS Lett. 386:115–122, Elsevier Science Publishers B.V., Amsterdam (1996).

Angliker, H. et al., "The synthesis of lysylfuoromethanes and their properties as inhibitors of trypsin, plasmin and cathespin B," Biochem J. 241:871–875, The Biochemical Society, London, England (1987).

Conaldi, P.G. et al., "HIV–1 Kills Renal Tubular Epithelial Cells In Vitro by Triggering an Apoptotic Pathway Involving Caspase Activation and Fas Upregulation," J. Clin. Invest. 102:2041–2049, The American Society for Clinical Investigation, Inc., New York, NY (Dec. 1998).

del Pozo, O., and Lam, E., "Caspases and programmed cell death in the hypersensitive response of plants to pathogens," Curr. Biol. 8:1129–1132, Current Biology Ltd., London, England (Oct. 1998).

di Giovine, F.S., and Duff, G.W., "Interleukin 1: the first interleukin," Immunology Today 11:13–14, Elsevier Science Publishers Ltd., Barking, England (1990).

Dinarello, C. A., "Interleukin–1 and Interleukin–1 Antagonism," Blood 77:1627–1652, American Society for Hematology, Philadelphia, PA (1991).

Dolle, R.E. et al., "$P_1$ Aspartate–Based Peptide α–((2, 6–Dichlorobenzoyl)oxy)methyl Ketones as Potent Time–Dependent Inhibitors of Interleukin–1β–Converting Enzyme," J. Med. Chem. 37:563–564, American Chemical Society, Washington, DC (1994).

Dolle, R.E. et al., "Aspartyl α–((1–Phenyl–3–(trifluoromethyl)–pyrazol–5–yl)oxy)methyl Ketones as Interleukin–1β Converting Enzyme Inhibitors. Significance of the $P_1$ and $P_3$ Amido Nitrogens for Enzyme–Peptide Inhibitor Binding," J. Med. Chem. 37:3863–3866, American Chemical Society, Washington, DC (1994).

Dolle R.E. et al., "Aspartyl α–((Diphenylphosphinyl)oxy)methyl Ketones as Novel Inhibitors of Interleukin–1β Converting Enzyme. Utility of the Diphenylphosphinic Acid Leaving Group for the Inhibition of Cysteine Proteases," J. Med. Chem. 38:220–222, American Chemical Society, Washington, DC (1995).

Ellis, R.E. et al., "Mechanisms and Functions of Cell Death," Ann. Rev. Cell Bio. 7:663–698, Annual Reviews, Palo Alto, CA (1991).

Emery, E. et al., "Apoptosis after traumatic human spinal cord injury," J. Neurosurg. 89:911–920, American Association of Neurological Surgeons, Charlottesville, VA (Dec. 1998).

Goldberg, Y.P. et al., "Cleavage of huntingtin by apopain, a proapoptotic cysteine protease, is modulated by the polyglutamine tract," Nature Genetics 13:442–449, Nature Publishing Co., New York, NY (1996).

Graybill, T.L. et al., "α–((Tetronoyl)oxy)– and α–((Tetramoyl)oxy)methyl Ketone Inhibitors of the Interleukin–1β Converting Enzyme (ICE)," Bioorg. Med. Chem. Lett. 7:41–46, Elsevier Science Ltd., Oxford, England (1997).

Greenberg, J.T. et al., "Programmed Cell Death in Plants: A Pathogen–Triggered Response Activated Coordinately with Multiple Defense Functions," Cell 77:551–563, Cell Press, Cambridge, MA (1994).

Grobmyer, S.R. et al., "Peptidomimetic Fluoromethylketone Rescues Mice from Lethal Endotoxic Shock," *Mol. Med.* 5:585–594, Johns Hopkins University Press, Baltimore, MD (Sep. 1999).

Hara, H. et al., "Inhibition of interleukin 1β converting enzyme family proteases reduces ischemic and excitotoxic neuronal damage," *Proc. Natl. Acad. Sci. USA* 94:2007–2012, National Academy of Sciences, Washington, DC (Mar. 1997).

Hiraoka, J. et al., "Participation of apoptosis in renal amyloidosis," *Jpn. J. Nephrol.* 40:276–283, Japanese Society of Nephrology, Tokyo, Japan (May 1998).

Hotchkiss, R.S. et al., "Prevention of lymphocyte cell death in sepsis improves survival in mice," *Proc. Natl. Acad. Sci. USA* 96:14541–14546, National Academy of Sciences, Washington, DC (Dec. 1999).

Jaeschke, H. et al., "Activation of Caspase 3 (CPP32)–Like Proteases Is Essential for TNF–α–Induced Hepatic Parenchymal Cell Apoptosis and Neutrophil–Mediated Necrosis in a Murine Endotoxin Shock Model," *J. Immun.* 160:3480–3486, American Association of Immunologists, Baltimore, MD (Apr. 1998).

Jones, R.A. et al., "Fas–Mediated Apoptosis in Mouse Hepatocytes Involves the Processing and Activation of Caspases," *Hepatology* 27:1632–1642, American Association for the Study of Liver Diseases, Philadelphia, PA (Jun. 1998).

Kermer, P. et al., "Inhibition of CPP32–Like Protease Rescues Axotomized Retinal Ganglion Cells from Secondary Cell Death In Vivo," *J. Neuroscience* 18:4656–4662, Society for Neuroscience, Washington, DC (Jun. 1998).

Kubo, S. et al., "Hepatocyte injury in tyrosinemia type 1 is induced by fumarylacetoacetate and is inhibited by caspase inhibitors," *Proc. Natl. Acad. Sci. USA* 95:9552–9557, National Academy of Sciences, Washington, DC (Aug. 1998).

Lepschy, J., "Acylierung von Oxazolinonen– (5) unter besonderer Berücksichtigung der Dakin–West–Reaktion trifunktioneller Aminosäuren," *Ph.D. Thesis*, Technischen Universität München (1971).

Lieberthal, W. et al., "Necrosis and Apoptosis in Acute Renal Failure," *Sem. Nephr.* 18:505–518, W.B. Saunders Company, Philadelphia, PA (Sep. 1998).

Lotem, J. and Sachs, L., "Differential suppression by protease inhibitors and cytokines of apoptosis induced by wild–type p53 and cytotoxic agents," *Proc. Natl. Acad. Sci. USA* 93:12507–12512, National Academy of Sciences, Washington, DC (1996).

Mattson, M.P. et al., "Amyloid β–peptide induces apoptosis–related events in synapses and dendrites," *Brain Res.* 807:167–176, Elsevier Science B.V., Amsterdam, Netherlands (Oct. 1998).

Maulik, N. et al., "Oxidative stress developed during the reperfusion of ischemic myocardium induces apoptosis," *Free Rad. Biol. & Med.* 24:869–875, Elsevier Science Inc., Tarrytown, NY (Mar. 1998).

Miller, P.E. et al., "Photoreceptor cell death by apoptosis in dogs with sudden acquired retinal degeneration syndrome," *Am. J. Vet. Res.* 59:149–152, American Veterinary Medical Association, Schaumburg, IL (Feb. 1998).

Miura, M. et al., "Induction of Apoptosis in Fibroblasts by IL–1β–Converting Enzyme, a Mammalian Homolog of the *C. elegans* Cell Death Gene ced–3," *Cell* 75:653–660, Cell Press, Cambridge, MA (1993).

Mjalli, A.M.M. et al., "Phenylalkyl Ketones as Potent Reversible Inhibitors of Interleukin–1β Converting Enzyme," *Bioorg. Med. Chem. Lett.* 3:2689–2692, Elsevier Science Ltd., Oxford, England (1993).

Mjalli, A.M.M. et al., "Activated Ketones as Potent Reversible Inhibitors of Interleukin–1β Converting Enzyme," *Bioorg. Med. Chem. Lett.* 4:1965–1968, Elsevier Science Ltd., Oxford, England (1994).

Mjalli, A.M.M. et al., "Inhibition of Interleukin–1β Converting Enzyme by N–acyl–aspartic acid ketones," *Bioorg. Med. Chem. Lett.* 5:1405–1408 Elsevier Science Ltd., Oxford, England (1995).

Mjalli, A.M.M. et al., "Inhibition of Interleukin–1β Converting Enzyme by N–acyl–aspartyl Aryloxymethyl Ketones," *Bioorg. Med. Chem Lett.* 5:1409–1414, Elsevier Science Ltd., Oxford, England (1995).

Mosley, B. et al., "The Interleukin–1 Receptor Binds the Human Interleukin–1α Precursor but Not the Interleukin–1β Precursor," *J. Biol. Chem.* 262:2941–2944, American Society of Biological Chemists, Inc., Baltimore, MD (1987).

Mundle, S.D. et al., "Evidence for Involvement of Tumor Necrosis Factor–β in Apoptotic Death of Bone Marrow Cells in Myelodysplastic Syndromes," *Am. J. Hemat.* 60:36–47, Wiley–Liss, Inc., New York, NY (Jan. 1999).

Okamoto, Y. et al., "Peptide Based Interleukin–1β Converting Enzyme (ICE) Inhibitors: Synthesis, Structure Activity Relationships and Crystallographic Study of the ICE–Inhibitor Complex," *Chem. Pharm. Bull.* 47:11–21, Pharmaceutical Society of Japan, Tokyo, Japan (Jan. 1999).

Oppenheim, J.J. et al., "There is more than one interleukin 1," *Immun. Today* 7:45–56, Elsevier Science Publishers B.V., Amsterdam, Netherlands (1986).

Orrenius, S., "Apoptosis: molecular mechanisms and implications for human disease," *J. Internal Medicine* 237:529–536, Blackwell Science Ltd., Oxford, England (1995).

Ortiz, A. et al., "Cyclosporine A induces apoptosis in murine tubular epithelial cells: Role of caspases." *Kidney Int'l.* 54:S–25–S–29, International Society of Nephrology, Amsterdam, Netherlands (Dec. 1998).

Peleg, S. et al., "1,25–Dihydroxyvitamin $D_3$ and its analogs inhibit acute myelogenous leukemia progenitor proliferation by suppressing interleukin–1β production," *Chemical Abstracts 127*, Abstract No. 315124p, American Chemical Society, Washington, DC (1997).

Rasnick, D., "Synthesis of Peptide Fluoromethyl Ketones and the Inhibition of Human Cathepsin B," *Anal. Biochem.* 149:461–465, Academic Press, New York, NY (1985).

Rauber, P. et al., "The synthesis of peptidylfuoromethanes and their properties as inhibitors of serine proteinases and cystein proteinases," *Biochem. J.* 239:633–640, The Biochemical Society, London, England (1986).

Revesz, L. et al., "Synthesis of P1 Aspartate–Based Peptide Acyloxymethyl and Fluoromethyl Ketones as Inhibitors of Interleukin–1β–Converting Enzyme," *Tet Lett.* 35:9693–9696, Elsevier Science Ltd., United Kingdom (1994).

Rich, D.H., "Inhibitors of aspartic proteinases," in *Proteinase inhibitors. Research monographs in cell and tissue physiology. vol. 12*, Barrett, A.J. and G. Salvesen, eds., Elsevier, Amsterdam, Holland, pp. 179–208 (1986).

Richberg, M.H. et al., "Dead cells do tell tales," *Curr. Op. Plant Bio.* 1:480–485, Elsevier Science Ltd., United Kingdom (Dec. 1998).

Rodriguez, I. et al., "Systemic Injection of a Tripeptide Inhibits the Intracellular Activation of CPP32–like Proteases In Vivo and Fully Protects Mice against Fas–mediated Fulminant Liver Destruction and Death," *J. Exp. Med.* 184:2067–2072, The Rockefeller University Press, New York, NY (1996).

Shaw, E. et al., "Peptidyl fluoromethyl ketones as thiol protease inhibitors," *Biomed. Biochim. Acta* 45:1397–1403, Academie Verlag, Berlin, Germany (1986).

Semple, G. et al., "Peptidomimetic Aminomethylene Ketone Inhibitors of Interleukin–1β–Converting Enzyme (ICE)," *Bioorg. Med. Chem. Lett.* 8:959–964, Elsevier Science Ltd., Oxford, England (1998).

Sheikh, M.S. et al., "Ultraviolet–irradiation–induced apoptosis is mediated via ligand independent activation of tumor necrosis factor receptor 1," *Oncogene* 17:2555–2563, Stockton Press, London, England (Nov. 1998).

Sleath, P.R. et al., "Substrate Specificity of the Protease That Pocesses Human Interleukin–1β," *J. Bio. Chem.* 265:14526–14528, American Society for Biochemistry and Molecular Biology, Inc., Baltimore, MD (1990).

Slomiany, B.L. et al., "Activation of Apoptotic Caspase–2 and Nitric Oxide Synthase–2 in Buccal Mucosa with Chronic Alcohol Ingestion," *Biochem. & Mol. Bio. Int'l.* 45:1199–1209, Academic Press, Sydney, Australia (Sep. 1998).

Steinberg, D., "Caspase Inhibitors. Molecules Sought For Treatment of Diverse Disorders," *Gen. Eng. News* 18:16, 38,51, Mary Ann Liebert, Inc., New York, NY (Jul. 1998).

Suzuki, A., "The Dominant Role of CPP32 Subfamily in Fas–Mediated Hepatitis," *Proc. Soc. Exp. Biol. Med.* 217:450–454, Society for Experimental Biology and Medicine, Cambridge, MA (Apr. 1998).

Thornberry, N.A. et al., "A novel heterodimeric cystein protease is required for interleukin–1β processing in monocytes," *Nature* 356:768–774, Nature Publishing Group, London, England (1992).

Thornberry, N.A. et al., "A Combinatorial Approach Defines Specificities of Members of the Caspase Family and Granzyme B," *J. Biol. Chem.* 272:17907–17911, American Society for Biochemistry and Molecular Biology, Inc., Baltimore, MD (1997).

Thornberry, N.A., "Caspases: key mediators of apoptosis," *Chem. Biol.* 5:R97–R103, Current Biology Ltd., London, England (May 1998).

Thornberry, N.A. et al., "Inactivation of Interleukin–1β Converting Enzyme by Peptide (Acyloxy)methyl Ketones," *Biochemistry* 33:3934–3940, American Chemical Society, Washington, DC (1994).

Wataya, Y. et al., "Cytotoxic mechanism of 1–(3–C–ethynyl–β–D–ribo–pentofuranosyl)cytosine (ECyd)," *Chemical Abstracts 132*, Abstract No. 273983p, American Chemical Society, Washington, DC (May 2000).

Weil, M. et al., "Is programmed cell death required for neural tube closure?" *Curr. Biol.* 7:281–284, Current Biology Ltd., London, England (Apr. 1997).

Wyllie, A.H. et al., "Cell Death: The Significance of Apoptosis," *Int. Rev. Cyt.* 68:251–306, Academic Press, Inc., New York, NY (1980).

Wyllie, A.H., "Cell death: a new classification separating apoptosis from necrosis," in *Cell Death in Biology and Pathology*, Bowen and Lockin, eds., Chapman and Hall, New York, NY, pp. 9–34 (1981).

Xue, D. et al., "The Time Course for Infarction in a Rat Model of Transient Focal Ischemia," *Stroke* 21:166, Abstract No. 36, American Heart Association, Baltimore, MD (1990).

Yuan, J. et al., "The *C. elegans* Cell Death Gene ced–3 Encodes a Protein Similar to Mammalian Interleukin–1β–Converting Enzyme," *Cell* 75:641–652, Cell Press, Inc., Cambridge, MA (1993).

International Search Report International Application No. PCT/US00/23566, mailed Dec. 12, 2000.

Cai, S.X. et al., U.S. patent application No. 09/527,225, filed Mar. 16, 2000.

Cai, S.X. et al., U.S. patent application No. 09/545,565, filed Apr. 7, 2000.

Keana, J.F.W. et al., U.S. patent application No. 09/653,279, filed Aug. 31, 2000.

Weber, E. et al., U.S. patent application No. 09/685,689, filed Oct. 11, 2000.

Farber A., et al., "A specific inhibitor of apoptosis decreases tissue injury after intestinal ischemia– reperfusion in mice," *J. Vascular Surg.* 30:752–760, Mosby–Year Book, St. Louis MO (1999).

Fukuzuka, K., et al., "Casapase–3–Dependent Organ Apoptosis Early After Burn Injury," *Ann. Surg.* 229:851–859, Lippincott Williams & Wilkins, Inc., Philadelphia PA (1999).

Iovanna, J.L., "Redifferentiation and Apoptosis of Pancreatic Cells During Acute Pancreatitis," *Int. J. Pancreatol.* 20:77–84, Humana Press Inc., Clifton, NJ (1996).

Sata, N., et al., "Supraphysiologic Concentrations of Cerulein Induce Apoptosis in the Rat Pancreatic Acinar Cell Line AR4–2J," *Pancreas* 19:76–82, Lippincott Williams & Wilkins, Inc., Philadelphia, PA (1999).

Springer, J.E., et al., "Activation of the caspase–3 apoptotic cascade in traumatic spinal cord injury," *Nat. Med.* 5:943–946, Nature Publishing Company, New York, NY (1999).

\* cited by examiner

SUBSTITUTED ALPHA-HYDROXY ACID CASPASE INHIBITORS AND THE USE THEREOF

CROSS REFERENCE TO RELATED APPLICATIONS

The present application claims the benefit of U.S. Provisional Application No. 60/151,077 filed on Aug. 27, 1999 and No. 60/158,373, filed on Oct. 12, 1999, the contents of which are fully incorporated by reference herein.

BACKGROUND OF THE INVENTION

1. Field of the Invention

This invention is in the field of medicinal chemistry. In particular, the invention relates to substituted α-hydroxy acids that are inhibitors of caspases. The invention also relates to the use of these substituted α-hydroxy acids for reducing or treating apoptotic cell death and/or reducing interleukin 1-β production.

2. Prior Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis et al., *Dev.* 112:591–603 (1991); Vaux et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34). A cell activates its internally encoded suicide program as a result of either internal or external signals. The suicide program is executed through the activation of a carefully regulated genetic program (Wylie et al., *Int. Rev. Cyt.* 68:251 (1980); Ellis et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

Mammalian interleukin-1β (IL-1β) plays an important role in various pathologic processes, including chronic and acute inflammation and autoimmune diseases (Oppenheim, J. H. et. al. *Immunology Today*, 7, 45–56 (1986)). IL-1β is synthesized as a cell associated precursor polypeptide (pro-IL-1β) that is unable to bind IL-1 receptors and is biologically inactive (Mosley et al., *J. Biol. Chem.* 262:2941–2944 (1987)). By inhibiting conversion of precursor IL-1β to mature IL-1β, the activity of interleukin-1 can be inhibited. Interleukin-1β converting enzyme (ICE) is a protease responsible for the activation of interleukin-1β (IL-1β) (Thornberry, N. A., et al., *Nature* 356:768 (1992); Yuan, J., et al., *Cell* 75:641 (1993)). ICE is a substrate-specific cysteine protease that cleaves the inactive prointerleukin-1 to produce the mature IL-1. The genes that encode for ICE and CPP32 are members of the mammalian ICE/Ced-3 family of genes which presently includes at least twelve members: ICE, CPP32/Yama/Apopain, mICE2, ICE4, ICH1, TX/ICH-2, MCH2, MCH3, MCH4, FLICE/MACH/MCH5, ICE-LAP6 and $ICE_{rel}III$. The proteolytic activity of this family of cysteine proteases, whose active site (a cysteine residue) is essential for ICE-mediated apoptosis, appears critical in mediating cell death (Miura et al., *Cell* 75:653–660 (1993)). This gene family has recently been named caspases (Alnernri, E. S. et. al. *Cell,* 87, 171 (1996), and Thornberry, N. A. et. al. *J. Biol. Chem.* 272, 17907–17911 (1997)) and divided into three groups according to its known functions. Table 1 summarizes these known caspases.

TABLE 1

| Enzyme* |
|---|
| Group I: mediators of inflammation |
| Caspase-1 (ICE) |
| Caspase-4 ($ICE_{rel}$-II, TX, ICH-2) |
| Caspase-5 ($ICE_{rel}$-III, TY) |
| Group II: effectors of apoptosis |
| Caspase-2 (ICH-1, mNEDD2) |
| Caspase-3 (apopain, CPP-32, YAMA) |
| Caspase-7 (Mch-3, ICE-LAP3, CMH-1) |
| Group III: activators of apoptosis |
| Caspase-6 (Mch2) |
| Caspase-8 (MACH, FLICE, Mch5) |
| Caspase-9 (ICE-LAP6, Mch6) |
| Caspase-10 |

IL-1 is also a cytokine involved in mediating a wide range of biological responses including inflammation, septic shock, wound healing, hematopoiesis and growth of certain leukemias (Dinarello, C. A., *Blood* 77:1627–1652 (1991); diGiovine et al., *Immunology Today* 11:13 (1990)).

Many potent caspase inhibitors have been prepared based on the peptide substrate structures of caspases. However, in contrast to their potency in vitro, there are few inhibitors with good efficacy ($IC_{50}$<1 μM) in whole-cell models of apoptosis have been reported (Thornberry, N. A. *Chem. Biol.* 5:R97–103 (1998)). Therefore the need exists for cell death inhibitors that are efficacious in whole-cell models of apoptosis and active in animal model of apoptosis. These inhibitors thus can be employed as therapeutic agents to treat disease states in which regulated cell death and the cytokine activity of IL-1 play a role.

WO 93/05071 discloses peptide ICE inhibitors with the formula:

wherein Z is an N-terminal protecting group; $Q_2$ is 0 to 4 amino acids such that the sequence $Q_2$-Asp corresponds to at least a portion of the sequence Ala-Tyr-Val-His-Asp (SEQ ID NO:2); and $Q_1$ comprises an electronegative leaving group.

WO 96/03982 discloses aspartic acid analogs as ICE inhibitors with the formula:

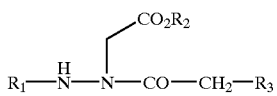

wherein $R_2$ is H or alkyl; $R_3$ is a leaving group such as halogen; $R_1$ is heteroaryl-CO or an amino acid residue.

U.S. Pat. No. 5,585,357 discloses peptidic ketones as ICE inhibitors with the formula:

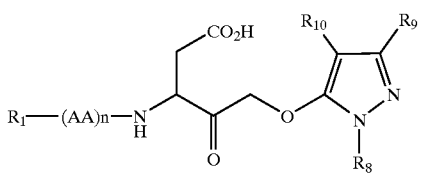

wherein n is 0–2; each AA is independently L-valine or L-alanine; $R_1$ is selected from the group consisting of N-benzyloxycarbonyl and other groups; $R_8$, $R_9$, $R_{10}$ are each independently hydrogen, lower alkyl and other groups.

Mjalli et al. (*Bioorg. Med. Chem. Lett.*, 3, 2689–2692, 1993) report the preparation of peptide phenylalkyl ketones as reversible inhibitors of ICE, such as:

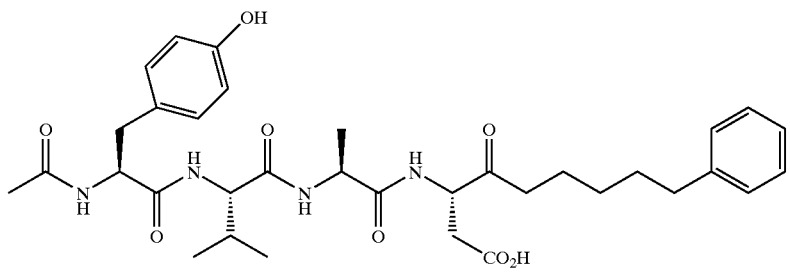

Thornberry et al. (*Biochemistry*, 33, 3934–3940, 1994) report the irreversible inactivation of ICE by peptide acyloxymethyl ketones:

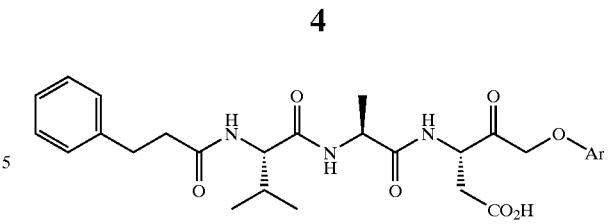

wherein Ar is COPh-2,6-$(CF_3)_2$, COPh-2,6-$(CH_3)_2$, Ph—$F_5$ and other groups.

Dolle et al. (*J. Med. Chem.* 37, 563–564, 1994) report the preparation of $P_1$ aspartate-based peptide α-((2,6-dichlorobenzoyl)oxy)methyl ketones as potent time-dependent inhibitors of ICE, such as:

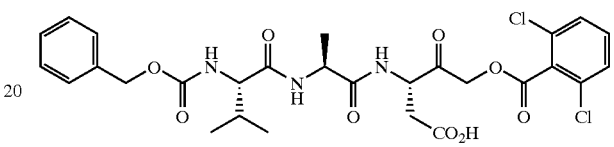

Mjalli et al. (*Bioorg. Med. Chem. Lett.*, 4, 1965–1968, 1994) report the preparation of activated ketones as potent reversible inhibitors of ICE:

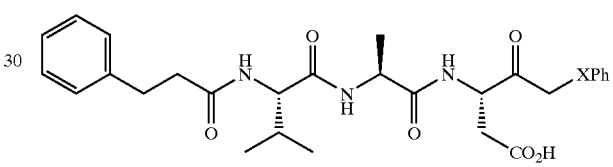

wherein X is $NH(CH_2)_2$, $OCO(CH_2)_2$, $S(CH_2)_3$ and other groups.

Dolle et al. (*J. Med. Chem.* 37, 3863–3866, 1994) report the preparation of α-((1-phenyl-3-(trifluoromethyl)-pyrazol-5- yl)oxy)methyl ketones as irreversible inhibitor of ICE, such as:

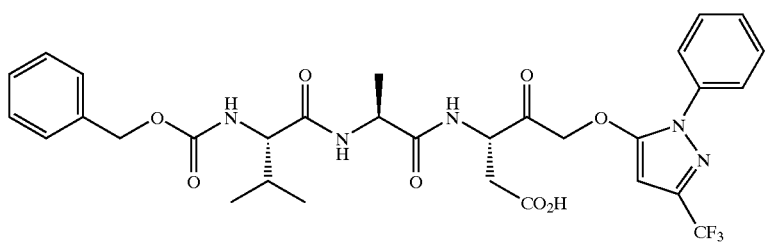

Mjalli et al. (*Bioorg. Med. Chem. Lett.*, 5, 1405–1408, 1995) report inhibition of ICE by N-acyl-Aspartic acid ketones:

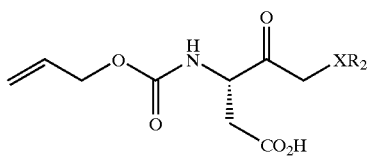

wherein $XR_2$ is $NH(CH_2)_2Ph$, $OCO(CH_2)_2cyclohexyl$ and other groups.

Mjalli et al. (*Bioorg. Med. Chem. Lett.*, 5, 1409–1414, 1995) report inhibition of ICE by N-acyl-aspartyl aryloxymethyl ketones, such as:

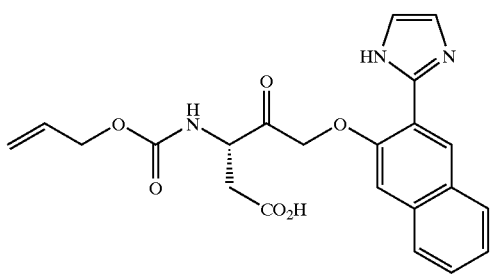

Dolle et al. (*J. Med. Chem.* 38, 220–222, 1995) report the preparation of aspartyl α-((diphenylphosphinyl)oxy)methyl ketones as irreversible inhibitors of ICE, such as:

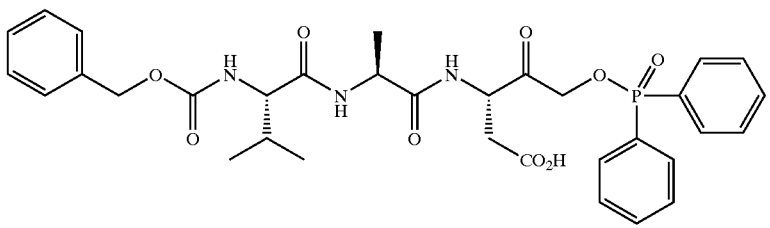

Graybill et al. (*Bioorg. Med. Chem. Lett.*, 7, 41–46, 1997) report the preparation of α-((tetronoyl)oxy)- and α-((tetramoyl)oxy)methyl ketones as inhibitors of ICE, such as:

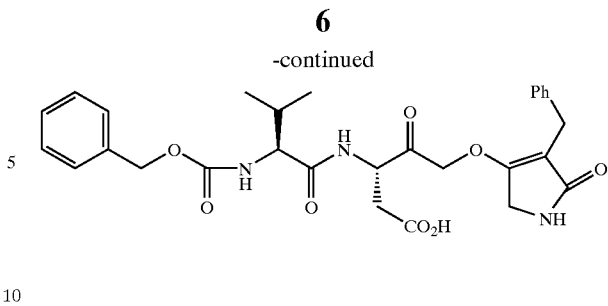

Semple et al. (*Bioorg. Med. Chem. Lett.*, 8, 959–964, 1998) report the preparation of peptidomimetic aminomethylene ketones as inhibitors of ICE, such as:

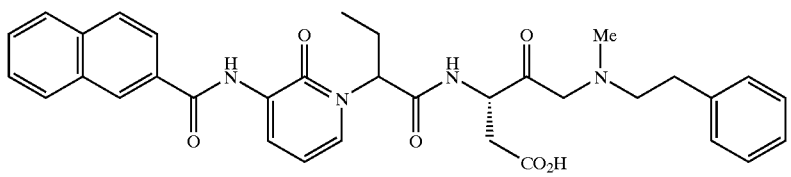

Okamoto et al. (*Chem. Pharm. Bull.* 47, 11–21, 1999) report the preparation of peptide based ICE inhibitors with the P1 carboxyl group converted to an amide, such as:

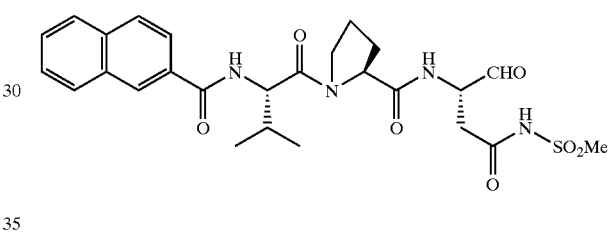

EP618223 patent application disclosed inhibitor of ICE as anti-inflammatory agents:

$$R-A_1-A_2-X-A_3$$

Wherein R is a protecting group or optionally substituted benzyloxy; $A_1$ is an α-hydroxy or α-amino acid residue or a radical of formula:

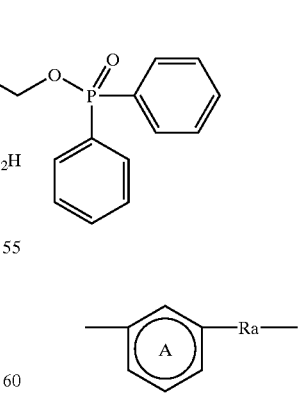

wherein ring A is optionally substituted by hydroxy or $C_{1-4}$ alkoxy and $R_a$ is CO or CS; $A_2$ is an α-hydroxy or α-amino acid residue or $A_1$ and $A_2$ form together a pseudo-dipeptide or a dipeptide mimetic residue; X is a residue derived from Asp; $A_3$ is $-CH_2-X_1-CO-Y_1$, $-CH_2-O-Y_2$, —CH$_2$—S—Y$_3$, wherein X$_1$ is O or S; Y$_1$, Y$_2$ or Y$_3$ is cycloaliphatic residue, and optionally substituted aryl.

WO99/18781 discloses dipeptides of formula:

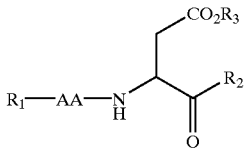

wherein R$_1$ is an N-terminal protecting group; AA is a residue of any natural or non-natural α-amino acid, β-amino acid, derivatives of an α-amino acid or β-amino acid; R$_2$ is H or CH$_2$R$_4$ where R$_4$ is an electronegative leaving group, and R$_3$ is alkyl or H, provided that AA is not His, Tyr, Pro or Phe. These dipeptides are surprisingly potent caspase inhibitors of apoptosis in cell based systems. These compounds are systemically active in vivo and are potent inhibitors of antiFas-induced lethality in a mouse liver apoptosis model and have robust neuroprotective effects in a rat model of ischemic stroke.

WO 99/47154 discloses dipeptides of formula:

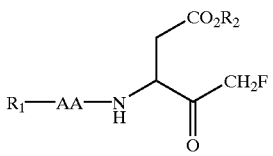

wherein R$_1$ is an N-terminal protecting group; AA is a residue of a non-natural α-amino acid or β-amino acid; R$_2$ is an optionally substituted alkyl or H.

WO 00/01666 discloses c-terminal modified oxamyl dipeptides as inhibitors of the ICE/ced-3 family of cysteine proteases:

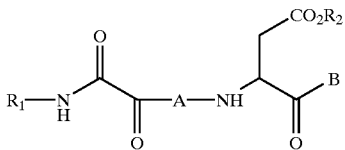

wherein A is a natural or unnatural amino acid; B is a hydrogen atom, a deuterium atom, alkyl, cycloalkyl and other groups; R$_1$ is alkyl, cycloalkyl and other groups, R$_2$ is hydrogen, lower alkyl and other groups.

WO 00/23421 discloses (substituted)acyl dipeptidyl inhibitors of the ICE/ced-3 family of cysteine proteases:

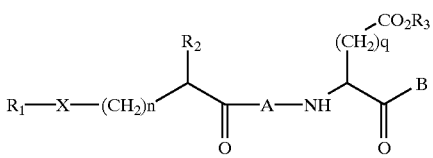

wherein A is a natural or unnatural amino acid; B is a hydrogen atom, a deuterium atom, alkyl, cycloalkyl and other groups; X is CH$_2$, C=O, O, S, NH, C=ONH or CH$_2$OC=ONH; n is 0, 1, or 2; q is 1 or 2; R$_1$ is optionally substituted aryl and heteroaryl; R$_2$ is hydrogen, alkyl and other groups; R$_3$ is hydrogen, alkyl and other groups.

WO 00/32620 discloses gamma-ketoacid tetrapeptides as inhibitors of the caspase-3:

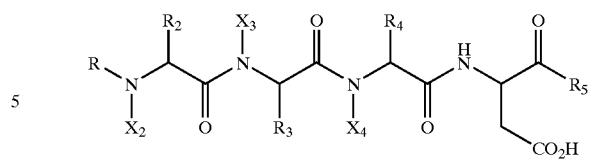

wherein R is H and COR$_1$; R$_1$ is hydrogen, alkoxy and other groups; R$_2$ is hydrogen, CH$_3$ and other groups; R$_3$ is hydrogen, CH$_3$ and other groups; R$_4$ is hydrogen, CH$_3$ and other groups; R$_5$ is C$_{1-6}$alkyl, arylC$_{1-6}$alkyl and other groups; X$_2$, X$_3$ and X$_4$ are independently H or X$_2$ and R$_2$, X$_3$ and R$_3$ or X$_4$ and R$_4$ may together form a saturated monocyclic ring.

SUMMARY OF THE INVENTION

The invention relates to compound of Formula I:

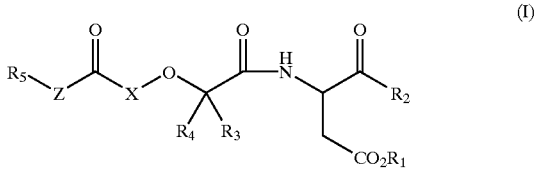

or pharmaceutically acceptable salts or prodrugs thereof, wherein

R$_1$ is an optionally substituted alkyl or hydrogen;

R$_2$ is hydrogen or optionally substituted alkyl;

R$_3$ and R$_4$ independently are hydrogen, optionally substituted aryl, optionally substituted heterocyclic, optionally substituted carbocyclic, optionally substituted heteroaryl, optionally substituted alkyl, optionally substituted alkenyl, or optionally substituted alkynyl;

R$_5$ is optionally substituted alkyl, optionally substituted carbocyclic, optionally substituted heterocyclic, optionally substituted aryl or optionally substituted heteroaryl;

Z is O, S, NR$_8$, or (CR$_9$R$_{10}$)$_n$, where R$_8$, R$_8$ and R$_{10}$ independently are hydrogen, alkyl or cycloalkyl, and n is 0, 1, 2, or 3; and X is a peptide of 1–2 amino acids or a bond.

The present invention provides pharmaceutical compositions comprising a compound of Formula I in an effective amount to reduce apoptotic cell death in an animal.

The invention relates to the discovery that the compounds represented by Formula I are inhibitors of caspases. The invention also relates to the use of the compounds of the invention for reducing, preventing or treating maladies in which apoptotic cell death is either a causative factor or a result. Examples of uses for the present invention include treating or ameliorating cell death in the central or peripheral nervous system, retinal neurons, cardiac muscle or immune system cells of an animal; treating or preventing polycystic kidney disease, renal amyloidosis, acute renal failure, cyclosporine A induced murin tubular epithelial cell death, HIV-induced nephropathy or anemia/erythropoiesis in an animal; protecting a mammalian organ or tissue from cell death due to deprivation of normal blood supply; reducing or preventing cell death in a donor organ or tissue after it has been transplanted into a host due to the effects of host immune cells; reducing or preventing the death of mammalian sperm or eggs used in in vitro fertilization procedures;

extending the lifespan of a mammalian or yeast cell line; treating or ameliorating hair loss or premature graying of the hair in a mammal; treating or ameliorating skin damage of a mammal due to exposure to high levels of radiation, heat or chemicals; treating or ameliorating sepsis in an animal; treating or ameliorating hepatitis in an animal; treating or ameliorating hereditary tyrosinemia type 1 in an animal; treating or ameliorating chronic alcohol ingestion induced buccal mucosa cell death in an animal; treating or ameliorating cell death in plants or flowers; treating or ameliorating radiation or ultraviolet-irradiation induced cell death in an animal; treating or ameliorating apoptotic death of bone marrow cells in myelodysplastic syndromes (MDS); treating or ameliorating apoptotic cell death in acute pancreatitis; treating or preventing the inflammatory response in psoriasis or inflammatory bowel disease; treating or ameliorating organ apoptosis after burn injury; treating or ameliorating small bowel tissue injury after intestinal ischemia-reperfusion; and treating, ameliorating or preventing oral mucositis, gastrointestinal mucositis, bladder mucositis, proctitis, bone marrow cell death, skin cell death or hair loss resulting from chemotherapy or radiation therapy of cancer in an animal

DETAILED DESCRIPTION OF THE INVENTION

The inhibitors of caspases and apoptotic cell death of the present invention are compounds having the general Formula I:

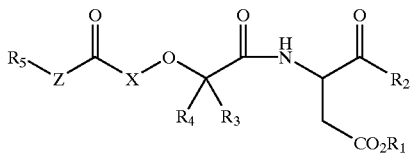

or pharmaceutically acceptable salts or prodrugs thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted carbocyclic, optionally substituted heteroaryl, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond. Where X is one amino acid, it may be any one of the common 20 amino acids e.g., Ala, Val, Leu, Ile, Pro, Phe, Trp, Met, Gly, Ser, Thr, Cys, Tyr, Asp, Asn, Glu, Asn, Lys, Arg and His. Where X is a peptide, it may be Asp-Glu, Asp-Ala, Asp-Phe, Val-Glu, Leu-Glu, Thr-Glu, Ile-Glu, Tyr-Glu, and Trp-Glu.

With respect to $R_1$, preferred alkyl groups are $C_{1-6}$ alkyl groups, e.g. methyl, ethyl, propyl, isopropyl, isobutyl, pentyl and hexyl groups; and substituted $C_{1-6}$alkyl groups, e.g. $CH_2O$ $CH_3$ and $CH_2OCOCH_3$ (AM).

Preferred $R_2$ are alkyl group substituted by electronegative group or leaving group, including fluoromethyl, chloromethyl, alkoxymethyl, aryloxymethyl, heteroaryloxymethyl, alkylthiomethyl, arylthiomethyl, aminomethyl, acyloxymethyl, and arylacyloxymethyl. Other examples of optional substituents that may be present at the $R_2$ alkyl group include, without limitation, 3-pyrazolyloxy optionally substituted at the 2, 4 and 5-positions with lower alkyl; 3-(1-phenyl-3-trifluoromethyl)pyrazolyloxy; 2,6-di(trifluoromethyl)benzoyloxy; 2,6-dimethylbenzoyloxy, pentafluoro-phenoxy; 2,6-dichlorobenzoyloxy; 2-(3-(2-imidazolyl)naphthyl)oxy; diphenylphosphinyloxy; tetronyloxy; and tetramoyloxy.

With respect to $R_3$ and $R_4$, preferred groups are those that will match the side chain of natural amino acids or non-natural amino acids. In one embodiment, preferred $R_3$ is hydrogen, preferred $R_4$ is straight-chained or branched $C_{1-6}$ alkyl including methyl, ethyl, isopropyl and isobutyl; or preferred $R_4$ is cycloalkyl, aryl or heteroaryl; or preferred $R_4$ is straight-chained or branched $C_{1-6}$ alkyl optionally substituted by one or more hydroxy, halogen, carboxy, amino, amide, ester, guanadino, thiol, alkylthiol, aryl, heterocyclic or heteroaryl groups.

With respect to $R_5$, preferred alkyl are methyl, ethyl, isopropyl, isobutyl; preferred substituents on alkyl are hydroxy, carboxy, halogen, $C_4$–$C_7$ cycloalkyl, saturated and unsaturated heterocyclic, aryl or heteroaryl; preferred cycloalkyl are cyclopentyl and cyclohexyl; preferred saturated and unsaturated heterocyclic groups are piperidinyl and morpholinyl; preferred aryls are phenyl and naphthyl; preferred heteroaryls are pyridyl, indolyl, furyl and thienyl; preferred substituents on the aryl and heteroaryl are methyl, ethyl, chloro, fluoro, bromo, trifluoromethyl, methoxy, hydroxy, carboxy, cyano and nitro. Especially preferred $R_5$ is optionally substituted phenyl, naphthyl, heteroaryl, or benzyl. Preferred Z is O, NH, or $CH_2$.

The invention relates to the discovery that the compounds represented by Formula I are inhibitors of caspases. These inhibitors slow or block cell death in a variety of clinical conditions and industrial applications in which the loss of cells, tissues or entire organs occurs. Therefore, the invention is also related to methods of treating, preventing or reducing conditions in which apoptosis plays a role. These conditions are more fully described below.

The methods comprise administering to an animal in need of such treatment an inhibitor of the present invention, or a pharmaceutically acceptable salt or prodrug thereof, in an amount effective to inhibit apoptotic cell death.

Preferred embodiments of the compounds of Formula I that may be employed as inhibitors of caspases are represented by Formula II:

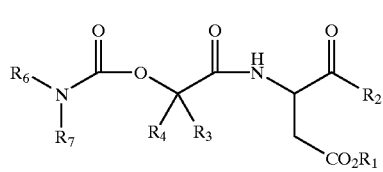

or pharmaceutically acceptable salts or prodrugs thereof wherein $R_1$–$R_4$ are as defined previously with respect to Formula I. $R_6$ and $R_7$ independently are hydrogen, alkyl, optionally substituted alkyl, $C_4$–$C_7$ cycloalkyl, saturated or unsaturated heterocyclic, aryl, heteroaryl, or $R_6$ and $R_7$ are combined together with the nitrogen to form a heterocycle.

Preferred $R_1$ is H, Me, Et, t-Bu or AM. Preferred $R_2$ is fluoromethyl, acyloxymethyl, arylacyloxymethyl, aryloxymethyl, heteroaryloxymethyl and aminomethyl.

With respect to $R_6$ and $R_7$, preferred alkyl are methyl, ethyl, isopropyl, isobutyl; preferred substituents on alkyl are hydroxy, carboxy, carbamyl, carboxy ester, halogen, $C_4$–$C_7$ cycloalkyl, saturated and unsaturated heterocyclic, aryl or heteroaryl; preferred cycloalkyl are cyclopentyl and cyclohexyl; preferred saturated and unsaturated heterocyclic groups are piperidinyl and morpholinyl; preferred aryls are phenyl and naphthyl; preferred heteroaryls are pyridyl, indolyl, furyl and thienyl; preferred substituents on the aryl and heteroaryl are methyl, ethyl, chloro, fluoro, bromo, trifluoromethyl, methoxy, hydroxy, carboxy, cyano and nitro. Preferred heterocycles from combination of $R_6$ and $R_7$ together with the nitrogen are piperidine, mopholine, and piperazine.

With respect to $R_3$ and $R_4$, preferred $R_3$ is hydrogen, and preferred $R_4$ are those that will match the side chain of natural amino acids or non-natural amino acids. Specifically, preferred $R_3$ and $R_4$, together with the attached carbon, oxygen and carbonyl group are a residue of an α-hydroxy acid. These α-hydroxy acids include, but are not limited to 3-methoxymandelic acid, 4-methoxymandelic acid, 2-methoxymandelic acid, 4-bromomandelic acid, 4-methylmandelic acid, 2,5-dimethylmandelic acid, 4-methylthiomandelic acid, 4-chloromandelic acid, 3-chloromandelic acid, 2-chloromandelic acid, 4-fluoromandelic acid, 2,3-difluoromandelic acid, 2,4-difluoromandelic acid, 2,5-difluoromandelic acid, 3,5-difluoromandelic acid, 3,4-difluoromandelic acid, 2,6-difluoromandelic acid, 2,3,5-trifluoromandelic acid, 2,3,6-trifluoromandelic acid, 3,4-methylenedioxymandelic acid, 4-trifluoromethylmandelic acid, 3-nitromandelic acid, 4-nitromandelic acid, mandelic acid, hexahydromandelic acid, 2-hydroxy-3-methylbutyric acid, 2-hydroxy-3,3-dimethylbutyric acid, 2-hydroxy-4-phenylbutyric acid, 2-hydroxybutyric acid, 2-hydroxybutynoic acid, 2-hydroxy-4-(methylthio)butyric acid, 2-hydroxy-3-butenoic acid, 2-hydroxy-3-methylpentanoic acid, 2-hydroxy-4-methylpentanoic acid, 3-phenyllactic acid, lactic acid, 3-chlorolactic acid, 3-imidazolelactic acid, 3,3,3-trifluorolactic acid, 3,3-difluoro-3-(4-fluorophenyl)lactic acid, 3,3-difluoro-3-(4-methoxyphenyl)lactic acid, 3,3-difluoro-3-(4-chlorophenyl)lactic acid, 3,3-difluoro-3-phenyllactic acid, 3-(1-naphthoxy)lactic acid, leucic acid, glycolic acid, 2-hydroxycaproic acid, 2-hydroxyvaleric acid, 2-hydroxyoctanoic acid, and indole-3-lactic acid. These α-hydroxy acids are commercial available from Aldrich, Sigma, Lancaster, Maybridge and other companies.

Exemplary preferred inhibitors of caspases having Formular I and II include, without limitation:
1-(Carbonyl-Asp-CH$_2$F)ethyl N-phenylcarbamate,
1-(Carbonyl-Asp-CH$_2$F)ethyl N-benzylcarbamate,
2-Methyl-1-(carbonyl-Asp-CH$_2$F)propyl N-phenylcarbamate,
2-Methyl-1-(carbonyl-Asp-CH$_2$F)propyl N-benzylcarbamate,
2-Methyl-1-(carbonyl-Asp-CH$_2$F)propyl N-(2,6-dichlorophenyl)carbamate,
2-Methyl-1-(carbonyl-Asp-CH$_2$F)propyl N-(2,5-dichlorophenyl)-carbamate,
2-Methyl-1-(carbonyl-Asp-CH$_2$F)propyl N-(2,4-dichlorophenyl)-carbamate,
2-Methyl-1-(carbonyl-Asp-CH$_2$DCB)propyl N-phenylcarbamate,
2-Methyl-1-(carbonyl-Asp-CH$_2$DCB)propyl N-(2,6-dichlorophenyl)-carbamate,
2-Methyl-1-(carbonyl-Asp-CH$_2$PTP)propyl N-phenylcarbamate,
2-Methyl-1-(carbonyl-Asp-CH$_2$PTP)propyl N-(2,6-dichlorophenyl)-carbamate,
2-Methyl-1-(carbonyl-Asp-CH$_2$DPP)propyl N-phenylcarbamate,
2-Methyl-1-(carbonyl-Asp-CH$_2$DPP)propylN-(2,6-dichlorophenyl)-carbamate,
2-Methyl-1-(carbonyl-Asp-CH$_2$F)propyl N-(2-methyl-1-methoxycarbonyl-propyl)carbamate,
2-Methyl-1-(carbonyl-Asp-CH$_2$F)propyl N-(3-fluorophenyl)carbamate,
2-Methyl-1-(carbonyl-Asp-CH$_2$F)propyl N-(4-fluorophenyl)carbamate,
2-Methyl-1-(carbonyl-Asp-CH$_2$F)propyl N-(3,4-difluorophenyl)carbamate,
2-Methyl-1-(carbonyl-Asp-CH$_2$F)propyl N-(4-phenoxyphenyl)carbamate,
1-(Carbonyl-Asp-CH$_2$F)propyl N-phenylcarbamate,
1-(Carbonyl-Asp-CH$_2$F)butyl N-phenylcarbamate,
1-(Carbonyl-Asp-CH$_2$F)-2-propenyl N-phenylcarbamate,
2-(4-Imidazolyl)-1-(carbonyl-Asp-CH$_2$F)ethyl N-phenylcarbamate,
2-Phenyl-1-(carbonyl-Asp-CH$_2$F)ethyl N-phenylcarbamate,
2-Methyl-1-(carbonyl-Asp-CH$_2$F)butyl N-phenylcarbamate,
3-Methyl-1-(carbonyl-Asp-CH$_2$F)butyl N-phenylcarbamate,
1-Phenyl-1-(carbonyl-Asp-CH$_2$F)methyl N-phenylcarbamate,
1-(2-Chlorophenyl)-1-(carbonyl-Asp-CH$_2$F)methyl N-phenylcarbamate,
1-(4-Chlorophenyl)-1-(carbonyl-Asp-CH$_2$F)methyl N-phenylcarbamate,
1-Cyclohexyl-1-(carbonyl-Asp-CH$_2$F)methyl N-phenylcarbamate,
2-Chloro-1-(carbonyl-Asp-CH$_2$F)ethyl N-phenylcarbamate,
2,2,2-Trifluoro-1-(carbonyl-Asp-CH$_2$F)ethyl N-phenylcarbamate, and
Z-Valine 2-methyl-1-(carbonyl-Asp-CH$_2$F)propyl ester.
where Z is benzyloxycarbonyl, DPP is diphenylphosphinyloxy, PTP is 1-phenyl-3-(trifluoromethyl)pyrazol-5-yloxy and DCB is 2,6-dichlorobenzoyloxy.

Useful aryl groups are $C_{6-14}$ aryl, especially $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups include straight chained and branched $C_{2-10}$ alkenyl groups, more preferably $C_{2-6}$ alkenyl groups. Typical $C_{2-10}$ alkenyl groups include ethenyl, propenyl, isopropenyl, butenyl, pentenyl, hexenyl and octenyl groups.

Useful alkynyl groups include straight chained and branched $C_{2-10}$ alkynyl groups, more preferably $C_{2-6}$ alkynyl groups. Typical $C_{2-10}$ alkynyl groups include ethynyl, propynyl, butynyl, pentynyl, hexynyl and octynyl groups.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl, chloromethyl, chlorofluoromethyl and trichloromethyl groups.

Useful alkoxy groups include oxygen substituted by one of the $C_{1-10}$ alkyl groups mentioned above.

Useful alkylthio groups include sulphur substituted by one of the $C_{1-10}$ alkyl groups mentioned above. Also included are the sulfoxides and sulfones of such alkylthio groups.

Useful acylamino groups are any $C_{1-6}$ acyl (alkanoyl) attached to an amino nitrogen. e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. formyloxy, acetoxy, propionoyloxy, butanoyloxy, pentanoyloxy, hexanoyloxy and the like.

Useful arylacyloxy groups include any of the aryl groups mentioned above substituted on any of the acyloxy groups mentioned above, e.g. 2,6-dichlorobenzoyloxy, 2,6-difluorobenzoyloxy and 2,6-di-(trifluoromethyl)-benzoyloxy groups.

Useful amino groups include —$NH_2$, —$NHR_{11}$, and —$NR_{11}R_{12}$, wherein $R_{11}$ and $R_{12}$ are $C_{1-10}$ alkyl or cycloalkyl groups as defined above.

Useful saturated or partially saturated heterocyclic groups include tetrahydrofuranyl, pyranyl, piperidinyl, piperizinyl, pyrrolidinyl, irnidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include any one of the following: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Optional substituents include one or more alkyl; halo; haloalkyl; cycloalkyl; aryl optionally substituted with one or more lower alkyl, halo, haloalkyl or heteroaryl groups; aryloxy optionally substitued with one or more lower alkyl, halo, haloalkyl or heteroaryl groups; aralkyl; heteroaryl optionally substitued with one or more lower alkyl, haloalkyl and aryl groups; heteroaryloxy optionally substitued with one or more lower alkyl, haloalkyl and aryl groups; alkoxy; alkylthio; arylthio; amino; acyloxy; arylacyloxy optionally substitued with one or more lower alkyl, halo alkyl and aryl groups; diphenylphosphinyloxy optionally substituted with one or more lower alkyl, halo or haloalkyl groups; heterocyclo optionally substitued with one or more lower alkyl, haloalkyl and aryl groups; heterocycloalkyloxy optionally substitued with one or more lower alkyl, haloalkyl and aryl groups; partially unsaturated heterocycloalkyl optionally substitued with one or more lower alkyl, haloalkyl and aryl groups; or partially unsaturated heterocycloalkyloxy optionally substitued with one or more lower alkyl, haloalkyl and aryl groups.

Certain of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy and Tris(hydroxymethyl) aminomethane (TRIS, tromethane).

Examples of prodrugs include compounds of Formulae I-II wherein $R_1$ is an alkyl group or substituted alkyl group such as $CH_2OCH_3$ and $CH_2OCOCH_3$ (AM ester).

The invention is also directed to a method for treating disorders responsive to the inhibition of caspases in animals suffering thereof. Particular preferred embodiments of compounds for use in the method of this invention are represented by previously defined Formulae I-II.

The compounds of this invention may be prepared using methods known to those skilled in the art. Specifically, compounds of Formulae I-II with a fluoromethyl ($CH_2F$) group can be prepared as illustrated by exemplary reactions in Scheme 1. Reaction of hydroxy acid with phenyl isocyanate gave the carbamate protected acid. Coupling of the acid with the intermediate hydroxy amine (Revesz et al., *Tetrahedron Lett.* 35:9693–9696 (1994)) produced the amide. Oxidation of the hydroxy group by Dess-Martin reagent according to Revesz et al. (*Tetrahedron Lett.* 35:9693–9696 (1994)) gave the ketone as a mixture of diasteriomers. Other oxidation reagents can be used in place of Dess-Martin reagent include pyridinium chlorochromate (PCC). TFA catalyzed cleavage of the t-Bu ester produced the acid.

Scheme 1

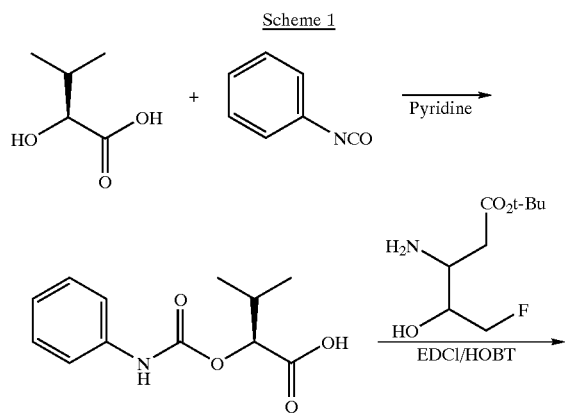

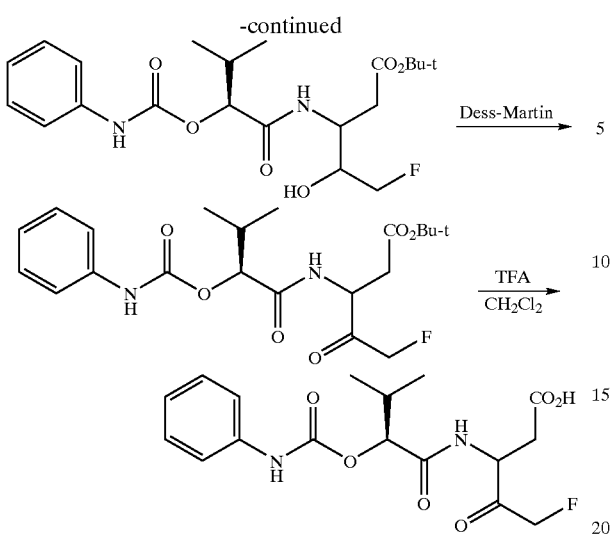

Compounds of Formulae I-II with a dichlorobenzoyloxy (DCB) group can be prepared as illustrated by exemplary reactions in Scheme 2. Reaction of the bromomethylketone with dichlorobenzoic acid gave the ester. The Z protecting group was removed by hydrogenation to give the amine, which was coupled with the acid to produce the amide. The t-Bu ester was cleaved by TFA to give the acid.

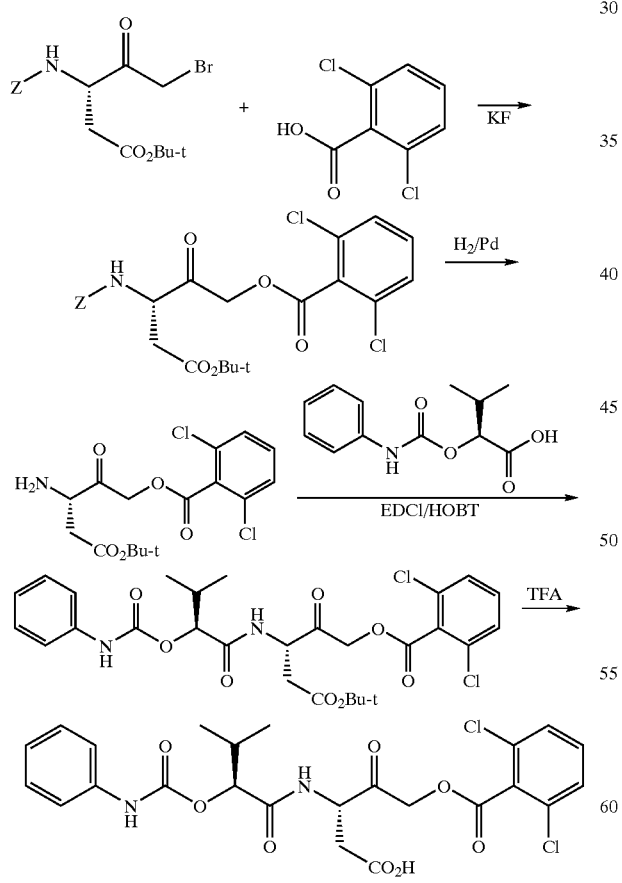

Similarly, compounds of Formulae I-II with a 1-phenyl-3-(trifluoromethyl)pyrazol-5-yloxy (PTP) and a diphenylphosphinyloxy (DPP) group can be prepared as illustrated by exemplary reactions in Scheme 3 and 4, respectively.

Scheme 3

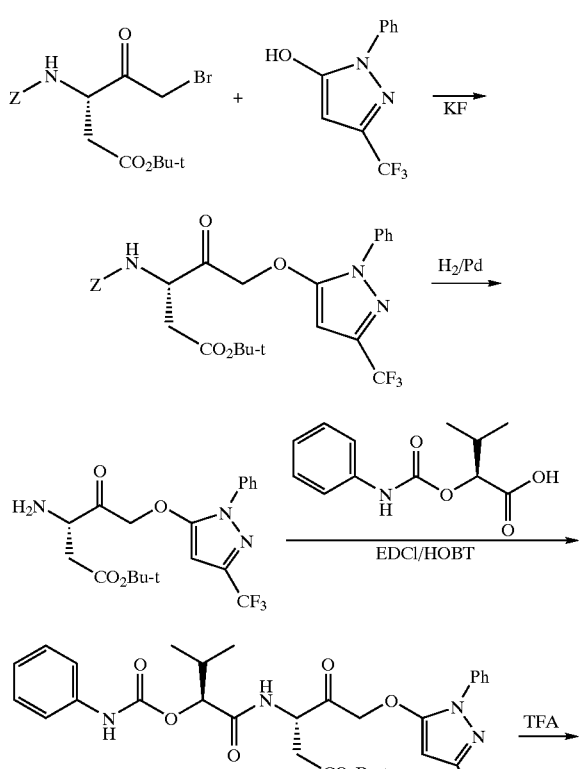

Scheme 4

-continued

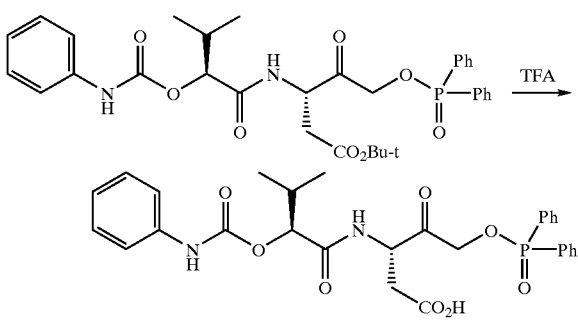

An important aspect of the present invention is the discovery that compounds having Formulae I-II are inhibitors of caspases. Therefore, these inhibitors are expected to slow or block cell death in a variety of clinical conditions in which the loss of cells, tissues or entire organs occurs.

The cell death inhibitors of the present invention can be used to reduce or prevent cell death in the nervous system (brain, spinal cord, and peripheral nervous system) under various conditions of ischemia and excitotoxicity, including, but not limited to, focal ischemia due to stroke and global ischemia due to cardiac arrest, as well as spinal cord injury (Emery et al., *J. Neurosurgery* 89:911–920 (1998) and Springer et al., *Nat Med.* 5:943–946 (1999)). One particular usage is to treat the effects of oxygen deprivation which can occur during the birth of infants in high-risk labors or drowning. The cell death inhibitors can also be used to reduce or prevent cell death in the nervous system due to traumatic injury (such as head trauma), viral infection or radiation-induced nerve cell death (for example, as a side-effect of cancer radiotherapy). The cell death inhibitors can also be used to reduce or prevent cell death in a range of neurodegenerative disorders, including but not limited to Alzheimer's disease (Mattson et al., *Brain Res.* 807:167–176 (1998)), Huntington's Disease, Parkinson's Disease, a prion disease, multiple sclerosis, amyotrophic lateral sclerosis, and spinobulbar atrophy. The in vivo neuroprotective properties of cell death inhibitors of the invention can be tested in a rat transient focal brain ischemia model (Xue et al., *Stroke* 21:166 (1990)).

The cell death inhibitors can also be used to treat or ameliorate cell death in the central or peripheral nervous system due to acute bacterial meningitis.

The cell death inhibitors of the invention can be used to reduce or prevent cell death in any conditions which potentially results in the death of cardiac muscle (Black et al., *J. Mol. Cel. Card.* 30:733–742 (1998) and Maulik et al., *Free Radic. Biol. Med.* 24:869–875 (1998)). This includes myocardial infarction due to myocardial ischemia and reperfusion, congestive heart failure and cardiomyopathy. One particular application is to reduce or prevent myocardial cell death as occurs in certain viral infections of the heart.

The in vivo activity of the cell death inhibitors of the invention can be tested using the "mouse liver apoptosis" model described by Rodriguez et al. (Rodriguez et al., *J. Exp. Med.* 184:2067–2072 (1996)). In this model, mice are treated intravenously (IV) with an antiFas antibody which induces massive apoptosis in the liver and other organs, leading to generalized organ failure and death. This model is useful for indirectly testing the systemic bioavailability of the cell death inhibitors of the invention, as well as their in vivo anti-apoptotic properties. The cell death inhibitors of the invention therefore can be used to reduce or prevent apoptosis of liver cells (Jones et al., *Hepatology* 27:1632–1642 (1998)) such as in sepsis (Jaeschke et al., *J. Immunol.* 160:3480–3486 (1998)) and hereditary tyrosinemia type 1 (HT1) (Kubo et al., *Proc. Natl. Acad. Sci. USA* 95:9552–9557 (1998)). The cell death inhibitors of the invention also can be used to treat hepatitis (Suzuki, *Proc. Soc. Exp. Biol. Med.* 217:450–454 (1998)).

The cell death inhibitors of the invention can be used to reduce or prevent cell death of retinal neurons (Kermer et al., *J. Neurosci.* 18:4656–4662 (1998) and Miller et al., *Am. J. Vet. Res.* 59:149–152 (1998)) as can occur in disorders which increase intraocular pressure (such as glaucoma) or retinal disorders associated with the aging process (such as age-related macular degeneration). The inhibitors can also be used to treat hereditary degenerative disorders of the retina, such as retinitis pigmentosa.

The cell death inhibitors of the invention can also be used to reduce or prevent cell death in the kidney. This includes renal amyloidosis (Hiraoka et al., *Nippon Jinzo Gakkai Shi* 40:276–83 (1998)), acute renal failure (Lieberthal et al. *Semin Nephrol.* 18:505–518 (1998)), murine tubular epithelial cell death induced by cyclosporine A (Ortiz et al. *Kidney International Supp.* 68:S25–S29 (1998)) and HIV-induced nephropathy (Conaldi et al. *J. Clin. Invest.* 102:2041–2049 (1998)).

The cell death inhibitors of the invention can also be used to reduce or prevent cell death of buccal mucosa due to chronic alcohol ingestion (Slomiany et al., *Biochem. Mol. Biol. Int.* 45:1199–1209 (1998)).

The cell death inhibitors of the invention can also be used to reduce or prevent apoptotic cell death in acute pancreatitis (Iovanna, Int. *J. Pancreatol.* 20:77–84 (1996) and Sata et al., *Pancreas* 19:76–82 (1999)).

The cell death inhibitors of the invention can also be used to reduce or prevent cell death in plants (Richberg et al., *Curr. Opin. Plant Biol.* 1:480–485 (1998)), such as plant cell death due to pathogens (Pozo et al., *Curr. Biol.* 8:1129–1132 (1998) and Greenberg et al., *Cell,* 77:551–563 (1994)).

The cell death inhibitors of the invention can also be used to reduce or prevent cell death due to radiation and ultraviolet-irradiation (Sheikh et al., *Oncogene* 17:2555–2563 (1998)).

The cell death inhibitors of the invention can also be used to reduce or prevent apoptotic death of bone marrow cells in myelodysplastic syndromes (MDS) (Mundle et al., *Am. J. Hematol.* 60:36–47 (1999)).

The cell death inhibitors of the invention can also be used to reduce or prevent organ apoptosis, such in thymus and spleen, in the early period after burn injury (Fukuzuka et al., *Ann. Surg.* 229:851–858 (1999)).

The cell death inhibitors of the invention can also be used to reduce or prevent premature death of cells of the immune system, and are particularly useful in treating immune deficiency disorders, such as acquired immune deficiency syndrome (AIDS), severe combined immune deficiency syndrome (SCIDS) and related diseases. The cell death inhibitors can also be used to treat radiation-induced immune suppression.

The cell death inhibitors can also be used to treat or ameliorate an autoimmune disorder including lupus erythematosus, rheumatoid arthritis and type I diabetes.

Transplantation of human organs and tissues is a common treatment for organ failure. However, during the transplantation process, the donor organ or tissue is at risk for cell death since it is deprived of its normal blood supply prior to being implanted in the host. This ischemic state can be treated with cell death inhibitors by infusion into the donor organ or tissue, or by direct addition of the cell death inhibitors to the organ/tissue storage medium, i.e. bathing the organ or tissue in the storage medium containg the compound prior to transplant of the organ or tissue into a mammal. Cell death inhibitors may also be administered to animals to reduce or prevent cell death in the donor organ/tissue after it has been transplanted to protect it from the effects of host immune cells which kill their targets by triggering apoptosis. Examples of such organs and tissues include without limitation kidneys, livers, hearts, pancreases, lungs, corneas, hands, and embryonic nigral tissue.

The cytoprotective effects of cell death inhibitors can also be used to prevent the death of human or animal sperm and eggs used in in vitro fertilization procedures. These inhibitors can be used during the harvesting process and can also be included in the storage medium.

Mammalian cell lines, insect cells and yeast cells are commonly used to produce large amounts of recombinant proteins (such as antibodies, enzymes or hormones) for industrial or medicinal use. The lifespan of some of these cell lines is limited due to growth conditions, the nature of the recombinant molecule being expressed (some are toxic) and other unknown factors. The lifespans of industrial cell lines can be extended by including these cell death inhibitors in the growth medium in a concentration range of 1–100 $\mu$M.

The factors governing hair growth and loss are largely unknown. There is some evidence, however, that hair follicle regression (referred to as catagen) may be due at least partially to apoptosis. Therefore, it is contemplated that the cell death inhibitors of the present invention can be used to treat hair loss that occurs due to various conditions, including but not limited to male-pattern baldness, radiation-induced or chemotherapy-induced hair loss, and hair loss due to emotional stress, by administering the inhibitors to the hair or hair follicles of an animal. There is also evidence that apoptosis may play a role in the loss of hair color. Therefore, it is contemplated that the cell death inhibitors of the present invention can also be used in treating or preventing cases of premature graying of the hair.

The death of skin epithelial cells can occur after exposure to high levels of radiation, heat or chemicals. It is contemplated that the cell death inhibitors of the present invention can be used to treat, reduce or prevent this type of skin damage. In one particular application, the cell death inhibitors can be applied as part of a topical formulation, e.g. an ointment, to the skin of an animal to treat acute overexposure to the sun and to prevent blistering and peeling of the skin.

Goldberg et al. (*Nature Genetics* 13:442–449 (1996)) reported recently that huntingtin, a protein product of Huntington's disease (HD) gene, can be cleaved by CPP32 but not ICE. The mutation underlying HD is an expansion of a CAG trinucleotide at the 5' end of the HD gene. The trinucleotide expansion exceeding 36 repeats is associated with the clinical presentation of HD. The CAG expansion promotes cleavage of huntingtin by CPP32, thus links the role of CPP32 in the apoptotic cell death in HD. Compounds of the present invention with CPP32 inhibiting activity are useful in blocking CPP32 induced apoptotic cell death, thus in preventing and treating HD and other disorders characterized by expansion of trinucleotide repeats such as myotonic dystrophy, fragile X mental retardation, spinobulbar muscular atrophy, spinocerebellar atoxia type I and Dentato-Rubro pallidoluysian atrophy.

The cell death inhibitors can also be used to treat or ameliorate small bowel tissue injury after intestinal ischemia-reperfusion, by administering to an animal in need thereof. See Farber, A. et al., *J. Vascular Surg.* 30:752–760 (1999).

The invention relates to a method of treating, ameliorating or preventing oral mucositis, gastrointestinal mucositis, bladder mucositis, proctitis, bone marrow cell death, skin cell death and hair loss resulting from chemotherapy or radiation therapy of cancer in an animal, comprising administering to the animal in need thereof an effective amount of a caspase inhibitor.

When animals are treated with chemotherapeutic agents and/or radiation to kill cancer cells, an unwanted side effect is the apoptotic death of rapidly dividing non-cancer cells. Such non-cancer cells include cells of the gastrointestinal tract, skin, hair, and bone marrow cells. According to the present invention, caspase inhibitors are administered to such non-cancer cells to prevent apoptosis of such cells. In a preferred embodiment, the caspase inhibitors are administered locally, e.g. to the gastrointestinal tract, mouth, skin or scalp to prevent apoptosis of the gastrointestinal, mouth, skin or hair cells but allowing for the death of the cancer cells. Thus, in one example, it is possible to treat brain cancer with chemotherapy or radiation therapy and protect the outer skin, hair cells, gastrointestinal tract and bone marrow by local administration of a caspase inhibitor. In the case of oral mucositis, the caspase inhibitor can be applied, for example, in the form of a mouth wash or mouth rinse, in a gel, or in the form of an oral slow release lozenge to prevent activation of caspases and apoptotic cell death induced by the chemotherapeutic agent or by radiation. In the case of gastrointestinal mucositis, the caspase inhibitor can be applied in a form such that it is not absorbed systemically or in a form that coats the surface of the gastrointestinal tract, or a suppository formulation for the treatment of gastrointestinal mucositis. In the case of proctitis, the capsase inhibitor may be applied as part of an enema or suppository. In the case of bladder mucositis, the caspase inhibitor may be applied though a bladder catheter. For prevention of radiation or chemotherapy-induced hair loss, the caspase inhibitor can be applied, for example, to the scalp in the form of a hair rinse, hair gel, shampoo or hair conditioner. Importantly, the caspase inhibitor can be applied prior to the administration of the chemotherapeutic agent or radiation, thus preventing or reducing the onset of the damaging effects of the chemotherapeutic agent or radiation to the normal cells.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for apoptosis-mediated disorders. e.g., neuronal cell death, heart disease, retinal disorders, polycystic kidney disease, immune system disorders and sepsis. Preferably, about 0.01 to about 10 mg/kg is orally administered to treat or prevent such disorders. For intramuscular injection, the dose is generally about one-half of the oral dose. For example, for treatment or prevention of neuronal cell death, a suitable intramuscular dose would be about 0.0025 to about 25 mg/kg, and most preferably, from about 0.01 to about 5 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular cell death inhibitors of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular cell death inhibitors of the present invention with a solution of a pharmaceutically acceptable non-toxic base such as sodium hydroxide, potassium hydroxide, choline hydroxide, sodium carbonate Tris and the like.

The pharmaceutical compositions of the invention may be administered to any animal which may experience the beneficial effects of the compounds of the invention. Foremost among such animals are mammals, e.g., humans, although the invention is not intended to be so limited.

The caspase inhibitors and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired. In general, the caspase inhibitors are administered locally to the tissues that are to be protected from apoptosis and separately from the chemotherapeutic agent. For example, cisplatin may be administered by i.v. injection to treat a cancer such as brain, lung, breast, liver, kidney, pancreatic, ovarian, prostatic cancer, and the caspase inhibitor administered locally to treat, ameliorate, or prevent apototic cell death in the mouth or gastrointestinal tract, such as a mouth wash for the treatment of oral mucositis; and IV injectable aqueous solution for the treatment of bone marrow cell death; and an oral formulation suitable for coating the gastrointestinal surfaces or an emema or suppository formulation for the treatment of gastrointestinal mucositis including proctitis. The caspase inhibitors may also be applied through a bladder catheter for the treatment, amelioration or prevention of bladder mucositis. Alternatively or concurrently, the caspase inhibitors may be applied topically to the skin and/or scalp to treat, ameliorate or prevent apoptotic cell death of hair and skin cells. In a further embodiment, the chemotherapeutic agent or radiation may be applied locally to treat a localized cancer such as brain, lung, breast, liver, kidney, pancreatic, ovarian, prostatic cancer, and the caspase inhibitor administered systemically, e.g. by i.v. injection, to treat, ameliorate or prevent apoptotic cell death of the gastrointestinal tract cells, mouth epithelial cells, bone marrow cells, skin cells and hair cells. In the case of oral mucositis in brain cancer treatment, for example, a caspase inhibitor that does not penetrate the blood-brain barrier can be applied, for example, systemically by i.v. injection followed by irradiation of the brain tumor. This would protect the oral mucosa from the harmful effects of radiation but the caspase inhibitor would not protect the brain tumor from the therapeutic effects of radiation. Importantly, the caspase inhibitor can be applied prior to administration of the radiation, thus preventing the onset of the damaging effects of the radiation to the normal mucosa cells.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin damage, such as that caused by exposure to high levels of radiation, including ultraviolet radiation, heat or chemicals.

One or more additional substances which have therapeutic effects on the skin may also be incorporated in the compositions. Thus, the composition may also contain one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are β-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include any compounds known to have a beneficial effect on skin. Such compounds include retinoids such as Vitamin A, in an amount of about 0.003–0.3% by weight and chromanols such as Vitamin E or a derivative thereof in an amount of about 0.1–10% by weight, both based on the weight of the composition. Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

In addition, these compositions may include other medicinal agents, growth factors, wound sealants, carriers, etc., that are known or apparent to those skilled in the art. The compositions of the invention are administered to a warm-blooded animal, such as human, already suffering from a skin damage, such as a burn, in an amount sufficient to allow the healing process to proceed more quickly than if the host were not treated. Amounts effective for this use will depend on the severity of the skin damage and the general state of health of the patient being treated. Maintenance dosages over a prolonged period of time may be adjusted as necessary. For veterinary uses, higher levels may be administered as necessary.

In the case of an animal suffering from decreased hair growth, the compositions of the invention are administered in an amount sufficient to increase the rate of hair growth. Amounts effective for this use will depend on the extent of decreased hair growth, and the general state of health of the patient being treated. Maintenance dosages over a prolonged period of time may be adjusted as necessary. For veterinary uses, higher levels may be administered as necessary.

When the compounds are to be administered to plants, they may be applied to the leaves and/or stems and/or flowers of the plant, e.g. by spraying. The compounds may be spayed in particulate form or dissolved or suspended in an appropriate carrier, e.g. in water or an oil-water emulsion. The compounds may also be combined with the soil of the plant. In this embodiment, the compounds are taken up by the roots of the plant.

In a preferred embodiment, the caspase inhibitor is formulated as part of a mouthwash for the treatment, amelioration or prevention of oral mucositis. Such mouthwashes are aqueous solutions of the caspase inhibitor which may also contain alcohol, glycerin, synthetic sweeteners and surface-active, flavoring and coloring agents. They may also contain anti-infective agents such as hexetidine and cetylpyridinium chloride. The mouthwashes may also contain topical anesthetics (e.g. benzocaine, cocaine, dyclonine hydrochloride, lidocaine, proparacaine hydrochloride or teracaine hydrochloride), for example, for relieving pain of radiation or chemotherapy-induced sores. The mouth washes may have either acidic or basic pH. See *Remington's Pharmaceutical Sciences*, A. R. Gennaro, ed., Mack Publishing Company (1990), pp. 1045, 1046, 1526 and 1965.

In another preferred embodiment, the caspase inhibitor is formulated as an oral formulation which is capable of coating the gastrointestinal surfaces for the treatment, amelioration or prevention of gastrointestinal mucositis. Examples of gastrointestinal mucositis include esophageal mucositis, gastric mucositis, and intestinal mucositis. Such formulations may comprise gastric antacids such as aluminum carbonate, aluminum hydroxide gel, bismuth subnitrate, bismuth subsalicylate, calcium carbonate, dihydroxyaluminum sodium carbonate, magaldrate, magnesium carbonate, magnesium hydroxide, magnesium oxide, sodium bicarbonate, milk of bismuth, dihydroxyaluminum aminoacetate, magnesium phosphate, magnesium trisilicate and mixtures thereof. Other additives include without limitation $H_2$-receptor antagonists, digestants, anti-emetics, adsorbants, and miscellaneous agents. See *Remington's Pharmaceutical Sciences*, A. R. Gennaro, ed., Mack Publishing Company (1990), pp. 774–778.

Chemotherapy agents such as cisplatin and radiation therapy often induce early and late onset emesis in the patient. Thus, in one embodiment an antiemetic is coadministered together with the caspase inhibitor to avoid emesis and retain contact of the caspase inhibitor with the gastrointestinal tract. Examples of such antiemetics include without limitation compounds that block the dopaminergic emetic receptors such as metoclopramide and trimethobenzamide, and cannabinoids. Metoclopramide may be administered orally prior to and/or during chemotherapy/radiation therapy/caspase inhibitor therapy to prevent the early emesis response and then later by intranasal administration according to U.S. Pat. Nos. 5,760,086 and 4,536,386 to prevent delayed onset emesis. During the period after chemotherapy/radiation therapy, both the caspase inhibitor and the antiemetic may be coadministered to treat, ameliorate or prevent gastrointestinal mucositis.

In a further embodiment, the caspase inhibitor may be formulated as an IV injectable solution for the treatment, amelioration or prevention of bone marrow cell death.

The compositions of the compositions may be administered to a warm-blooded animal, such as human, already suffering from chemotherapy or radiation therapy-induced non-cancer cell death, or, more preferably, before or during therapy with chemotherapy or radiation.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

S-1-(Carbonyl-Asp-$CH_2$F)ethyl N-Phenylcarbamate

Step A. t-Butyl 5-fluoro-3-[S-2-(phenylamino) carbonyloxypropionamido]-4-hydroxypentanoate. A mixture of S-(−)-2-[(phenylamino)carbonyloxy]propionic acid (201 mg, 0.96 mmol), EDCI (98 mg, 0.51 mmol), HOBT (74 mg, 0.48 mmol), DMAP (28 mg, 0.23 mmol) and t-butyl 3-amino-5-fluoro-4-hydroxypentanoate (101 mg, 0.49 mmol) in THF (6 mL) was stirred at room temperature for 17 h. It was diluted with 1:1 hexane/EtOAc (80 mL), washed with water, 2N HCl, water, saturated $NaHCO_3$, brine and dried over $Na_2SO_4$. The solution was evaporated and the residue was purified by flash chromatography (hexane/EtOAc 3/2) to give the title compound as a white solid (80 mg, 0.21 mmol, 43%). $^1$H NMR ($CDCl_3$): 7.40–7.05 (m, 6H), 5.18 (q, H=6.9, 1H), 4.54–3.95 (m, 4H), 2.75–2.51 (m, 2H), 1.51 (d, J=6.9, 3H), 1.42 (m, 9H).

Step B. 1-(Carbonyl-Asp(O-Bu-t)-$CH_2$F)ethyl N-phenylcarbamate. A mixture of periodinane (0.49 g, 1.16 mmol) and t-butyl 5-fluoro-3-[S-2-(phenylamino)carbonyloxypropionamido]-4-hydroxypentanoate (80 mg, 0.21 mmol) in dichloromethane (6 mL) was refluxed for 20 h. After cooled to room temperature, a saturated sodium bicarbonate aqueous solution (10 mL) containing 0.5 g of $Na_2S_2O_3$ was added. The resulting mixture was stirred for 1 h, extracted with 1:1 hexane/EtOAc (80 mL). The organic phase was washed with water and brine, dried over sodium sulfate and concentrated in vacuo to yield the title compound as a hydroscopic white solid (69 mg, 0.18 mmol, 85%). $^1$H NMR ($CDCl_3$): 7.40–7.25 (m, 5H), 7.13–7.00 (m, 2H), 5.30–4.87 (m, 4H), 3.05–2.71 (m, 2H), 1.56–1.53 (m, 3H), 1.42 (s, 9H).

Step C. 1-(Carbonyl-Asp-$CH_2$F)ethyl N-phenylcarbamate. To a solution of 1-(carbonyl-Asp(O-Bu-t)-$CH_2$F)ethyl N-phenylcarbamate (69 mg, 0.18 mmol) in 3 mL of $CH_2Cl_2$ was added 1 mL of TFA. The resulting solution was stirred at room temperature for 1 h, diluted with EtOAc (80 mL), neutralized with saturated $Na_2HPO_4$ to pH~5, washed with water and brine, dried over $Na_2SO_4$ and concentrated in vacuo to give the title compound as a white solid (26 mg, 0.078 mmol, 44%). $^1$H NMR (DMSO-$d_6$): 9.86 (br s, 1H), 8.67 (br s, 1H), 7.45–7.27 (m, 4H), 6.99 (br s, 1H), 5.30–4.80 (m, 4H), 4.59 (br s, 1H), 2.72 (br s, 2H), 1.37 (br s, 3H).

EXAMPLE 2

2-Methyl-1-(carbonyl-Asp-$CH_2$F)propyl N-Phenylcarbamate

Step A. 2-Phenylaminocarbonyloxy-3-methylbutyric acid. To a solution of 2-hydroxy-3-methylbutyric acid (0.20 g, 1.7 mmol) in pyridine (8 ml) was added phenyl isocyanate (0.184 mL). The resulting solution was stirred at room temperature for 4 h, acidified with 2N HCl to pH~2 and diluted with EtOAc (30 mL). The organic phase was isolated, washed with water and brine, dried over $Na_2SO_4$ and concentrated in vacuo. The residue was purified by chromatography (3:2 hexane/EtOAc then EtOAc) to yield the title compound as a colorless oil (200 mg, 0.85 mmol, 50%). $^1$H NMR (DMSO-$d_6$): 9.80 (s, 1H), 7.47 (d, J=7.8, 2H), 7.28 (t, J=7.8, 2H), 7.00 (t, J=7.8, 1H), 4.71 (d, J=4.2, 1H), 2.17 (m, 1H), 1.02–0.97 (m, 6H).

The title compound was prepared in three steps as described in Example 1 from 2-phenylaminocarbonyloxy-3-methylbutyric acid and t-butyl-3-amino-5-fluoro-4-hydroxypentanoate. $^1$H NMR (DMSO-$d_6$): 9.79 (s, 1H), 8.62 (s, 1H), 7.47 (d, J=7.8, 2H), 7.28 (t, J=7.8, 2H), 7.00 (t, J=7.8, 1H), 5.14–4.60 (m, 4H), 2.80–2.60 (m, 2H), 2.10 (m, 1H), 0.97–0.93 (m, 6H).

EXAMPLE 3

S-2-Methyl-1-(carbonyl-Asp-$CH_2$F)propyl N-Phenylcarbamate

The title compound was prepared in four steps as described in Examples 1 and 2 from S-(+)-2-hydroxy-3-methylbutyric acid and phenyl isocyanate. $^1$H NMR (DMSO-$d_6$): 9.79 (s, 1H), 8.60 (s, 1H), 7.47 (d, J=7.5, 2H), 7.28 (t, J=8.2, 2H), 7.00 (t, J=7.2, 1H), 5.14–4.58 (m, 4H), 2.80–2.71 (m, 2H), 2.10 (m, 1H), 0.98–0.93 (m, 6H).

EXAMPLE 4

S-1-(Carbonyl-Asp-$CH_2$F)ethyl N-Benzylcarbamate

The title compound was prepared in four steps as described in Examples 1 and 2 from L-(+)-lactic acid and benzyl isocyanate. $^1$H NMR (acetone-d$_6$): 7.81–7.00 (m, 7H), 5.37–4.33 (m, 6H), 2.89–2.67 (m, 2H), 1.40 (d, J=6.9, 3H).

EXAMPLE 5

2-Methyl-1-(carbonyl-Asp-CH$_2$F)propyl N-Benzylcarbamate

The title compound was prepared in four steps as described in Examples 1 and 2 from 2-hydroxy-3-methylbutyric acid and benzyl isocyanate. $^1$H NMR (DMSO-d$_6$): 12.48 (s, 1H), 8.59–8.51 (m, 1H), 7.90–7.80 (m, 1H), 7.33–7.24 (m, 5H), 5.34–4.99 (m, 2H), 4.70–4.29 (m, 3H), 4.18 (d, J=6.0, 2H), 2.85–2.53 (m, 2H), 2.01(m, 1H), 0.92–0.87 (m, 6H).

EXAMPLE 6

S-2-Methyl-1-(carbonyl-Asp-CH$_2$F)propyl N-Benzylcarbamate

The title compound was prepared in four steps as described in Examples 1 and 2 from S-(+)-2-hydroxy-3-methylbutyric acid and benzyl isocyanate. $^1$H NMR (DMSO-d$_6$): 8.46 (s, 1H), 7.86 (t, H=6.3, 1H), 7.34–7.21 (m, 5H), 4.97–4.56 (m, 4H), 4.18 (d, J=6.0, 2H), 2.68 (m, 2H), 2.02 (m, 1H), 0.91–0.86 (m, 6H).

EXAMPLE 7

S,S-2-Methyl-1-(carbonyl-Asp-CH$_2$F)propyl N-(2-Methyl-1-methoxycarbonylpropyl)-carbamate Step A. S,S-1-Carboxy-2-methylpropyl N-(2-methyl-1-methoxycarbonyl-propyl)-carbamate. To a solution of S-(+)-2-hydroxy-3-methylbutyric acid (0.2 g, 1.69 mmol) in pyridine (10 ml) was added methyl-(S)-(−)-2-isocyanato-3-methylbutyrate (0.243 mL, 1.69 mmol). The resulting solution was then stirred at room temperature for 24 h, acidified with 2N HCl to pH~2 and diluted with EtOAc (30 mL). The organic phase was isolated, washed with water and brine, and concentrated in vacuo. The residue was dissolved in saturated NaHCO$_3$, washed with 4:1 hexane: EtOAc. The aqueous phase was acidified with 2N HCl to pH~2, extracted with ethyl acetate (2×30 mL). The organic layer was combined and washed with water and brine, dried over Na$_2$SO$_4$ and concentrated in vacuo to yield the title compound as a colorless oil (92 mg, 0.334 mmol, 20%). $^1$H NMR (DMSO-d$_6$): 6.42 (d, J=8.7, 1H), 4.08–3.99 (m, 2H), 3.62 (d, J=0.9, 3H), 2.04–1.93 (m, 2H), 0.94–0.83 (m, 12H).

Step B. S,S-Methyl-1-(carbamyl-N-(t-butyl 5-fluoro-4-hydroxypentanoate-3-yl)propyl N-(2-methyl-1-methoxycarbonyl-propyl)carbamate. A mixture of S,S-1-carboxy-2-methylpropyl N-(2-methyl-1-methoxycarbonylpropyl)carbamate (92 mg, 0.335 mmol), EDCI (66 mg, 0.335 mmol), HOBt (45 mg, 0.335 mmol), DMAP (20 mg, 0.17 mmol) and tert-butyl-3-amino-5-fluoro-4-hydroxypentanoate (69 mg, 0.335 mmol) in THF (10 mL) was stirred at room temperature for 20 h, filtered and concentrated in vacuo. The residue was purified by chromatography (3:2 hexane/ EtOAc) to yield the title compound as a colorless oil (20 mg, 0.043 mmol, 13%). $^1$H NMR (CDCl$_3$): 6.98–6.86 (m, 1H), 5.50 (d, J=9.3, 1H), 5.10–5.05 (m, 1H), 4.90 (d, J=4.2, 1H), 4.50–4.00 (m, 5H), 3.76 (s, 3H), 2.74–2.48 (m, 2H), 2.33–2.13 (m, 2H), 1.44 (s, 9H), 0.99–0.93 (m, 12H).

Step C. S,S-2-Methyl-1-(carbonyl-Asp(OBu-t)CH$_2$F) propyl N-(2-methyl-1-methoxycarbonylpropyl)carbamate. A mixture of Dess-Martin reagent (0.2 g, 0.47 mmol) and S,S-2-methyl-1-(carbamyl-N-(t-butyl 5-fluoro-4-hydroxypentanoate-3-yl)propyl N-(2-methyl-1-methoxycarbonylpropyl)-carbamate (20 mg, 0.043 mmol) in dichloromethane (10 mL) was refluxed for 20 h, cooled to room temperature, and 25 mL of saturated sodium bicarbonate aqueous solution containing 0.2 g of Na$_2$S$_2$O$_3$ was added. The resulting mixture was stirred for 2 days, diluted with EtOAc (50 mL), washed with water and brine, dried over Na$_2$SO$_4$ and concentrated in vacuo. The residue was purified by chromatography (3:1 hexane/EtOAc) to yield the title compound as a colorless oil (12 mg, 0.026 mmol, 60%). 1H NMR (CDCl$_3$): 7.25–7.10 (m, 1H), 5.52–5.44 (m, 1H), 5.31–4.84 (m, 4H), 4.34–4.25 (m, 1H), 3.77 (d, J=1.2, 3H), 3.09–2.66 (m, 2H), 2.34–2.12 (m, 2H), 1.42 (d, J=1.8, 9H), 1.00–0.88 (m, 12H).

Step D. S,S-2-Methyl-1-(carbonyl-Asp-CH$_2$F)propyl N-(2-Methyl-1-methoxycarbonylpropyl)-carbamate. To a solution of S,S-2-methyl-1-(carbonyl-Asp(OBu-t)CH$_2$F) propyl N-(2-methyl-1-methoxycarbonylpropyl)-carbamate (12 mg, 0.026 mmol) in 1.5 mL of CH$_2$Cl$_2$ was added 0.5 mL of TFA. The resulting solution was allowed to stir at room temperature for 4 h, diluted with CHCl$_3$ (3×15 mL), concentrated in vacuo to give the title compound as a light yellow solid (10.25 mg, 0.025 mmol, 96%). $^1$H NMR (acetone-d$_6$): 7.75–7.40 (m, 1H), 6.85–6.82 (m, 1H), 5.34–5.12 (m, 1H), 4.84–4.80 (m, 2H), 4.58–4.43 (m, 1H), 4.18–4.11 (m, 1H), 3.71 (s, 3H), 2.88–2.60 (m, 2H), 2.16–2.05 (m, 2H), 0.98–0.86 (m, 12H).

EXAMPLE 8

S-2-Methyl-1-(carbonyl-Asp-CH2DCB)propyl N-Phenylcarbamate

Step A. Benzyloxycarbonyl-Asp(OBu-t)-CH$_2$DCB. To a mixture of benzyloxycarbonyl-Asp(OBu-t)-CH$_2$Br (300 mg, 0.75 mm), 2,6-dichlorobenzoic acid (215 mg, 1.12 mm) and KF (217 mg, 3.75 mm) was added anhydrous DMF (5 ml). The mixture was stirred under Ar at room temperature for 12 hours, and then was diluted with ethyl acetate (30 ml). The solution was washed with saturated aqueous ammonium chloride solution, brine, and then dried over Na$_2$SO$_4$. The solvent was removed, and the residue was purified with flash column chromatography (Hexane:EtOAc, 2:1). The title compound was obtained as a colorless oil (296 mg, 0.67 mm, 89%). $^1$H NMR (CDCl$_3$): 7.34 (m, 8H), 5.97(d, J=8.7, 1H), 5.21 (d, J=6.6, 2H), 5.16 (s, 2H), 4.70 (m, 1H), 2.90 (m, 2H), 1.28 (s, 9H).

Step B. S-2-Methyl-1-(carbonyl-Asp(OBu-t)-CH$_2$DCB) propyl N-phenylcarbamate. To a solution of benzyloxycarbonyl-Asp(OBu-t)-CH$_2$DCB (150 mg, 0.34 mm) in ethanol (20 ml) was added Pd/C (30 mg) and aqueous HCl (0.2 ml, 6N). The mixture was stirred under H2 for 3 h, and then the Pd/C was removed by filtration. The ethanol solution was concentrated, and the residue was carried on for the next reaction. A mixture of S-2-phenylaminocarbonyloxy-3-methylbutylic acid (81 mg, 0.34 mmol ), EDCI (65 mg, 0.34 mmol), HOBt (52 mg, 0.34 mmol), DMAP (24 mg, 0.20 mmol) and NH$_2$-Asp(OBu-t)-CH$_2$DCB-HCl in THF (10 mL) was stirred at room temperature for 16 h, and then diluted with ethyl acetate (30 ml). The solution was washed with aqueous NaOH (1 N), aqueous HCl (1 N), brine, and dried over Na$_2$SO$_4$. The solution was concentrated, and the residue was purified by flash column chromatography to give the title compound as a pale yellow solid (41 mg, 0.07 mm, 22%). $^1$H NMR (CDCl$_3$): 7.28 (m, 8H), 5.05 (m, 3H), 4.67 (m, 1H), 2.88 (m, 2H), 2.31 (m, 1H), 1.42 (s, 9H), 0.91 (m, 6H).

Step C. S-2-Methyl-1-(carbonyl-Asp-CH$_2$DCB)propyl N-phenylcarbamate. To a solution of 2-Methyl-1-(carbonyl-Asp(OBu-t)-CH$_2$DCB)propyl N-phenylcarbamate in CH$_2$Cl$_2$ (2 ml) was added TFA (1 ml). The mixture was stirred at 25° C. under Ar for 12 h, and then was diluted with ethyl acetate (30 ml). The solution was washed with saturated aqueous Na$_2$HPO$_4$, and dried over Na$_2$SO$_4$. It was evaporated and the residue was dried under vacuum. The title compound was obtained as yellow color solid (18 mg, 0.03 mm, 47%). $^1$H NMR (CDCl$_3$): 7.29 (m, 8H), 5.00 (m, 3H), 4.21 (m, 1H), 2.91 (m, 2H), 2.35 (m, 1H), 0.97 (m, 6H).

EXAMPLE 9

S-2-Methyl-1-(carbonyl-Asp-CH$_2$F)propyl N-(3-Fluorophenyl)carbamate

The title compound was prepared in four steps as described in Example 1 and 2 from S-(+)-2-hydroxy-3-methylbutyric acid and 3-fluorophenyl isocyanate. $^1$H NMR (DMSO-d$_6$): 10.09 (bs, 1H), 8.73 (m, 1H), 8.29 (m, 1H), 7.35 (m, 3H), 6.83 (s, 1H), 5.18 (m, 1H), 4.69 (m, 3H), 2.60 (m, 2H), 2.11 (m, 1H), 0.96 (m, 6H).

EXAMPLE 10

S-2-Methyl-1-(carbonyl-Asp-CH$_2$F)propyl N-(4-Fluorophenyl)carbamate

The title compound was prepared in four steps as described in Example 1 and 2 from S-(+)-2-hydroxy-3-methylbutyric acid and 4-fluorophenyl isocyanate. $^1$H NMR (DMSO-d$_6$): 9.73 (bs, 1H), 8.56 (bs, 1H), 7.33 (s, 2H), 7.00 (s, 2H), 5.05 (m, 1H), 4.55 (m, 3H), 2.52 (m, 2H), 1.97 (m, 1H), 0.81 (m, 6H).

EXAMPLE 11

S-2-Methyl-1-(carbonyl-Asp-CH$_2$F)propyl N-(3,4-Difluorophenyl)carbamate

The title compound was prepared in four steps as described in Example 1 and 2 from S-(+)-2-hydroxy-3-methylbutyric acid and 3,4-difluorophenyl isocyanate. $^1$H NMR (DMSO-d$_6$): 10.09 (bs, 1H), 8.65 (bs, 1H), 7.56 (m, 1H), 7.37 (m, 1H), 7.24 (m, 1H), 5.05 (m, 1H), 4.65 (m, 3H), 2.73 (m, 2H), 2.11 (m, 1H), 0.95 (m, 6H).

EXAMPLE 12

S-2-Methyl-1-(carbonyl-Asp-CH$_2$F)propyl N-(4-Phenoxyphenyl)carbamate

The title compound was prepared in four steps as described in Example 1 and 2 from S-(+)-2-hydroxy-3-methylbutyric acid and 4-phenoxyphenyl isocyanate. $^1$H NMR (DMSO-d$_6$): 12.45 (bs, 1H), 9.84 (bs, 1H), 8.65 (m, 1H), 7.48 (d, J=8.7 Hz, 2H), 7.35 (dd, J=7.5, 8.4 Hz, 2H), 7.08 (dd, J=7.2, 7.5 Hz, 2H), 6.95 (m, 3H), 5.22 (m, 1H), 4.69 (m, 3H), 2.62 (m, 2H), 2.09 (m, 1H), 0.93 (m, 6H).

EXAMPLE 13

S-1-Cyclochexyl-1-(carbonyl-Asp-CH$_2$F)methyl N-Phenylcarbamate

The title compound was prepared in four steps from (S)-(+)-hexahydromandelic acid and phenyl isocyanate by the method described in Example 1 and 2 as a white solid. $^1$H NMR (DMSO-d$_6$): 9.76 (bs, 1H), 8.68 (bs, 1H), 7.44–7.27 (m, 4H), 6.99 (bs, 1H), 5.30–4.80 (m, 4H), 1.80–1.45 (m, 6H), 1.14 (bs, 5H).

EXAMPLE 14

S-2-Methyl-1-(carbonyl-Asp-CH$_2$F)propyl N-(2,5-Dichloroyphenyl)carbamate

The title compound was prepared in four steps as described in Example 1 and 2 from S-(+)-2-hydroxy-3-methylbutyric acid and 2,5-dichlorophenyl isocyanate. $^1$H NMR (DMSO-d$_6$): 9.39 (s, 1H), 8.69 (bs, 1H), 7.75 (d, J=6.6 Hz, 1H), 7.52 (d, J=8.4 Hz, 1H), 7.24 (d, J=8.7 Hz, 1H), 5.19 (m, 1H), 4.72 (m, 3H), 2.75 (m, 2H), 2.10 (m, 1H), 0.93 (m, 6H).

EXAMPLE 15

S-2-Methyl-1-(carbonyl-Asp-CH$_2$F)propyl N-(2,4-Dichloroyphenyl)carbamate

The title compound was prepared in four steps as described in Example 1 and 2 from S-(+)-2-hydroxy-3-methylbutyric acid and 2,4-dichlorophenyl isocyanate. $^1$H NMR (CDCl$_3$): 8.10 (dd, J=8.7, 3.9 Hz,1H), 7.39 (m, 1H), 7.26 (m, 3H), 5.12 (m, 2H), 4.88 (m, 2H), 2.87 (m, 2H), 2.32 (m, 1H), 0.97 (m, 6H).

EXAMPLE 16

S-2-Methyl-1-(carbonyl-Asp-CH$_2$PTP)propyl N-Phenylcarbamate

The title compound was prepared in 3 steps as described in Example 8 from benzyloxycarbonyl-Asp(OBu-t)-CH$_2$Br and 5-hydroxy-1-phenyl-3-(trifluoromethyl)pyrazole. $^1$H NMR (CDCl$_3$): 7.72 (m, 1H), 7.32 (m, 10H), 7.17 (m, 2H), 5.08 (m, 3H), 4.86 (m, 1H), 2.81 (m, 2H), 2.31 (m, 1H), 1.03 (m, 6H).

EXAMPLE 17

Enzyme Activity

The activity of S-2-methyl-1-(carbonyl-Asp-CH$_2$F) propyl N-phenylcarbamate as an inhibitor of caspase-3 was measured in a fluorometric enzyme assay. Enzyme activity was measured using synthetic peptide substrates attached to a fluorogenic leaving group. Cleavage of the synthetic substrate by the enzyme results in a fluorescent signal which is read in a spectrofluorometer or in a fluorometric microtiter plate reader.

12 concentrations of the test compound ranging from 30 pM to 10 μM were tested in the enzyme assay. The enzyme reaction was conducted in the presence of 2 ng rcaspase 3 (purchased from PharMingen, a Becton division company, San Diego, Calif.), various concentrations of test compound, 10 μM caspase 3 substrate Ac-DEVD-AMC (SEQ ID NO:1, purchased from Quality Controlled Biochemicals, Inc. Hopkinton, Mass.) and caspase buffer (20 mM PIPES, 100 mM NaCl, 10 mM DTT, 1 mM EDTA, 0.1% CHAPS and 10% sucrose, pH 7.2) in a total volume of 100 μL. The enzyme reaction was carried out in a 96-well plate and incubated at 37° C. for 30 minutes. The plate was then read with a fluorescence plate reader (EG&G WALLAG 1420–002) using excitation filter at 355 nm/emission filter at 460 nm. The data were analyzed using GraphPrism software to give an IC$_{50}$ value of 17 nM for S-2-methyl-1-(carbonyl-Asp-CH$_2$F)propyl N-phenylcarbamate.

EXAMPLE 18

Cell Protection Activity

Cell protection activity was determined by examining the ability of S-2-methyl-1-(carbonyl-Asp-CH$_2$F)propyl N-phenylcarbamate to block HeLa cell death induced by TNF-α. In this assay, 25,000 HeLa cells are seeded in 96-well plates 24 hours prior to testing. On the assay day, the cells are pre-incubated for 30 minutes with the test compound at eight different concentrations and the cells are then challenged with TNF-α (25 ng/ml) and cycloheximide (30 μg/ml) and incubated further for 24 hours. The dead cells are then removed by two PBS washes and 100 μL of a cell-mass indicator solution (calcein AM, final concentration 8 μM) is added. After a 20 minute incubation, the fluorescent signal is measured at 485/510 nm and the data are expressed as percent control, using control cultures treated only with cycloheximide. In these experiments, the $EC_{50}$ of S-2-methyl-1-(carbonyl-Asp-$CH_2$F)propyl N-phenylcarbamate for cytoprotection is 150 nM.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

optionally substituted heteroaryl, optionally substituted carbocyclic, optionally substituted alkyl, optionally substituted alkenyl, or optionally substituted alkynyl; and $R_6$ and $R_7$ independently are hydrogen, alkyl, optionally substituted alkyl, $C_4$–$C_7$ cycloalkyl, heterocyclic, aryl, heteroaryl, or $R_6$ and $R_7$ are combined together with the nitrogen to form a heterocycle.

2. A compound according to claim 1, wherein $R_2$ is hydrogen, fluoromethyl, acyloxymethyl, arylacyloxymethyl, aryloxymethyl, heteroaryloxymethyl, or aminomethyl.

3. A compound according to claim 1, wherein $R_1$ is H, Me, Et or acetoxymethyl.

4. A compound according to claim 1, wherein $R_3$ is hydrogen and $R_4$ is straight-chained or branched $C_{1-6}$ alkyl, cycloalkyl, aryl or heteroaryl.

5. A compound according to claim 1, wherein $R_3$ is hydrogen and $R_4$ is straight-chained or branched $C_{1-6}$ alkyl optionally substituted by hydroxy, halogen, carboxy, amino, amide, ester, guanadino, thiol, alkylthiol, aryl, heterocyclic or heteroaryl.

6. A compound according to claim 1, wherein $R_6$ is hydrogen and $R_7$ is optionally substituted phenyl, naphthyl, heteroaryl or benzyl.

What is claimed is:

1. A compound having the Formula II:

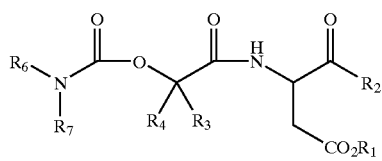

(II)

or a pharmaceutically acceptable salt or prodrug thereof wherein $R_1$ and $R_2$ independently are hydrogen or optionally substituted alkyl;

$R_3$ and $R_4$ independently are hydrogen, optionally substituted aryl, optionally substituted heterocyclic, 7. A compound according to claim 1, wherein $R_6$ is hydrogen and $R_7$ is an optionally substituted alkyl.

8. A compound selected from the group consisting of:
1-(Carbonyl-Asp-$CH_2$F)ethyl N-phenylcarbamate,
1-(Carbonyl-Asp-$CH_2$F)ethyl N-benzylcarbamate,
2-Methyl-1-(carbonyl-Asp-$CH_2$F)propyl N-phenylcarbamate,
2-Methyl-1-(carbonyl-Asp-$CH_2$F)propyl N-benzylcarbamate,
2-Methyl-1-(carbonyl-Asp-$CH_2$F)propyl N-(2,6-dichlorophenyl)carbamate,
2-Methyl-1-(carbonyl-Asp-$CH_2$F)propyl N-(2,5-dichlorophenyl)-carbamate,
2-Methyl-1-(carbonyl-Asp-$CH_2$F)propyl N-(2,4-dichlorophenyl)-carbamate,
2-Methyl-1-(carbonyl-Asp-$CH_2$DCB)propyl N-phenylcarbamate, 2-Methyl-1-(carbonyl-Asp-CH$_2$DCB)propyl N-(2,6-dichlorophenyl)-carbamate,
2-Methyl-1-(carbonyl-Asp-CH$_2$PTP)propyl N-phenylcarbamate,
2-Methyl-1-(carbonyl-Asp-CH$_2$PTP)propyl N-(2,6-dichlorophenyl)-carbamate,
2-Methyl-1-(carbonyl-Asp-CH$_2$DPP)propyl N-phenylcarbamate,
2-Methyl-1-(carbonyl-Asp-CH$_2$DPP)propyl N-(2,6-dichlorophenyl)-carbamate,
2-Methyl-1-(carbonyl-Asp-CH$_2$F)propyl N-(2-methyl-1-methoxycarbonyl-propyl)carbamate, and
Z-Valine 2-methyl-1-(carbonyl-Asp-CH$_2$F)propyl ester.

9. A compound selected from the group consisting of:
2-Methyl-1-(carbonyl-Asp-CH$_2$F)propyl N-(3-fluorophenyl)carbamate,
2-Methyl-1-(carbonyl-Asp-CH$_2$F)propyl N-(4-fluorophenyl)carbamate,
2-Methyl-1-(carbonyl-Asp-CH$_2$F)propyl N-(3,4-difluorophenyl)carbamate,
2-Methyl-1-(carbonyl-Asp-CH$_2$F)propyl N-(4-phenoxyphenyl)carbamate,
1-(Carbonyl-Asp-CH$_2$F)propyl N-phenylcarbamate,
1-(Carbonyl-Asp-CH$_2$F)butyl N-phenylcarbamate,
1-(Carbonyl-Asp-CH$_2$F)-2-propenyl N-phenylcarbamate,
2-(4-Imidazolyl)-1-(carbonyl-Asp-CH$_2$F)ethyl N-phenylcarbamate,
2-Phenyl-1-(carbonyl-Asp-CH$_2$F)ethyl N-phenylcarbamate,
2-Methyl-1-(carbonyl-Asp-CH$_2$F)butyl N-phenylcarbamate,
3-Methyl-1-(carbonyl-Asp-CH$_2$F)butyl N-phenylcarbamate,
1-Phenyl-1-(carbonyl-Asp-CH$_2$F)methyl N-phenylcarbamate,
1-(2-Chlorophenyl)-1-(carbonyl-Asp-CH$_2$F)methyl N-phenylcarbamate,
1-(4-Chlorophenyl)-1-(carbonyl-Asp-CH$_2$F)methyl N-phenylcarbamate,
1-Cyclohexyl-1-(carbonyl-Asp-CH$_2$F)methyl N-phenylcarbamate,
2-Chloro-1-(carbonyl-Asp-CH$_2$F)ethyl N-phenylcarbamate, and
2,2,2-trifluoro-1-(carbonyl-Asp-CH$_2$F)ethyl N-phenylcarbamate.

10. A pharmaceutical composition, comprising a compound of claim, 1, and a pharmaceutically acceptable carrier.

11. A method of inhibiting cell death of a cell or tissue, comprising contacting said cell or tissue with an effective amount of a compound of claim 1.

12. A method of treating or ameliorating cell death in the central or peripheral nervous system, retinal neurons, cardiac muscle or immune system cells of an animal, comprising administering to the animal in need of such treatment or ameliorating an effective amount of a compound of claim 1.

13. The method of claim 12, wherein said cell death is in the central or peripheral nervous system, and is due to one of:
(a) a condition of ischemia and excitotoxicity selected from the group consisting of focal ischemia due to stroke and global ischemia due to cardiac arrest;
(b) traumatic injury;
(c) viral infection;
(d) radiation-induced nerve cell death;
(e) a neurodegenerative disorder selected from the group consisting of Alzheimer's disease, Parkinson's Disease, a prion disease, multiple sclerosis, amyotrophic lateral sclerosis, and spinobulbar atrophy;
(f) spinal cord injury; or
(g) acute bacterial meningitis.

14. The method of claim 12, wherein said cell death is in the central or peripheral nervous system, and is due to expansion of trinucleotide repeats of the Huntington's Disease gene.

15. The method of claim 12, wherein said cell death is due to Huntington's Disease.

16. The method of claim 12, wherein said cell death is in cardiac muscle tissue, and is due to myocardial infarction, congestive heart failure, cardiomyopathy or viral infection of the heart.

17. The method of claim 12, wherein said cell death is in retinal neurons and is due to increased intraocular pressure, age-related macular degeneration or retinitis pigmentosa.

18. The method of claim 12, wherein said cell death is in the immune system, and is due to an immune deficiency disorder selected from the group consisting of acquired immune deficiency syndrome, severe combined immune deficiency syndrome and radiation-induced immune suppression.

19. The method of claim 12, wherein said cell death is due to an autoimmune disorder selected from the group consisting of lupus erythematosus, rheumatoid arthritis and type I diabetes.

20. The method of claim 12, wherein said cell death is due to type I diabetes.

21. A method of treating or preventing polycystic kidney disease, renal amyloidosis, acute renal failure, cyclosporine A induced murin tubular epithelial cell death, HIV-induced nephropathy or anemia/erythropoiesis in an animal, comprising administering to the animal in need of such treatment or preventing an effective amount of a compound of claim 1.

22. A method of protecting a mammalian organ or tissue from cell death due to deprivation of normal blood supply, comprising contacting said organ or tissue with an effective amount of a compound of claim 1.

23. The method of claim 22, wherein said organ or tissue is present in a storage medium prior to transplant into a mammal.

24. The method of claim 22, wherein said tissue is embryonic nigral tissue.

25. The method of claim 22, wherein said contacting comprises infusion of said compound into the organ or tissue, or bathing of said organ or tissue in a storage medium which comprises said compound.

26. A method of reducing or preventing cell death in a donor organ or tissue after it has been transplanted into a host due to the effects of host immune cells, comprising administering to said host in need thereof an effective amount of a compound of claim 1.

27. A method of reducing or preventing the death of mammalian sperm or eggs used in in vitro fertilization procedures, comprising contacting said sperm or egg with an effective amount of a compound of claim 1.

28. A method of extending the lifespan of a mammalian or yeast cell line, comprising contacting said cell line with a compound of claim 1.

29. The method of claim 28, wherein said contacting comprises including said compound in a cell growth medium.

30. A method of treating or ameliorating hair loss or premature graying of the hair in a mammal, comprising contacting the hair or hair follicles of the mammal in need thereof with a compound of claim 1.

31. The method of claim 30, wherein hair loss is treated, and said hair loss is due to male-pattern baldness, radiation, chemotherapy or emotional stress.

32. A method of treating or ameliorating skin damage of a mammal due to exposure to high levels of radiation, heat or chemicals, comprising applying to the skin of the mammal in need thereof with a compound of claim 1.

33. The method of claim 32, wherein said compound is applied as part of an ointment.

34. The method of claim 32, wherein said skin damage is due to acute over-exposure to the sun, and wherein said treating reduces blistering and peeling of the skin.

35. A method of treating or ameliorating sepsis in an animal, comprising administering to the animal in need thereof an effective amount of a compound of claim 1.

36. A method of treating or ameliorating hepatitis in an animal, comprising administering to the animal in need thereof an effective amount of a compound of claim 1.

37. A method of treating or ameliorating hereditary tyrosinemia type 1 in an animal, comprising administering to the animal in need thereof an effective amount of a compound of claim 1.

38. A method of treating or ameliorating chronic alcohol ingestion induced buccal mucosa cell death in an animal, comprising administering to the animal in need thereof an effective amount of a compound of claim 1.

39. A method of treating or ameliorating cell death in plants or flowers, comprising administering to the plants or flowers in need thereof an effective amount of a compound of claim 1.

40. A method of treating or ameliorating radiation or ultraviolet-irradiation induced cell death in an animal, comprising administering to the animal in need thereof an effective amount of a compound of claim 1.

41. A method of treating or ameliorating apoptotic death, of bone marrow cells in myelodysplastic syndromes (MDS), in an animal, comprising administering to the animal in need thereof an effective amount of a compound of claim 1.

42. A method of treating or ameliorating apoptotic cell death, in acute pancreatitis, in an animal, comprising administering to the animal in need thereof an effective amount of a compound of claim 1.

43. A method of treating or preventing the inflammatory response in psoriasis or inflammatory bowel disease, in an animal, comprising administering to the animal in need thereof an effective amount of a compound of claim 1.

44. A method of treating or ameliorating organ apoptosis, after burn injury, in an animal, comprising administering to the animal in need thereof an effective amount of a compound of claim 1.

45. A method of treating or ameliorating small bowel tissue injury, after intestinal ischemia-reperfusion, in an animal, comprising administering to the animal in need thereof an effective amount of a compound of claim 1.

46. A method of treating, ameliorating or preventing oral mucositis, gastrointestinal mucositis, bladder mucositis, proctitis, bone marrow cell death, skin cell death or hair loss resulting from chemotherapy or radiation therapy of cancer in an animal, comprising administering to the animal in need thereof an effective amount of a compound of claim 1.

47. The method of claim 46, wherein said compound is administered topically or orally.

48. The method of claim 47, wherein said compound is formulated as part of a mouthwash for the treatment, amelioration or prevention of oral mucositis.

49. The method of claim 47, wherein said compound is formulated as part of a slow release buccal lozenge.

50. The method of claim 47, wherein said compound is formulated as part of a suppository.

51. The method of claim 47, wherein said compound is formulated as part of a gel.

52. The method of claim 46, wherein said compound is administered through a bladder catheter for the treatment, amelioration or prevention of bladder mucositis.

53. The method of claim 46, wherein said compound is administered as part of an enema for the treatment, amelioration or prevention of proctitis.

54. The method of claim 46, wherein said compound is formulated as an oral formulation which is capable of coating the gastrointestinal surfaces for the treatment, amelioration or prevention of gastrointestinal mucositis.

55. The method of claim 54, wherein said gastrointestinal mucositis is esophageal mucositis, gastric mucositis, or intestinal mucositis.

56. The method of claim 46, wherein said compound is administered by i.v. injection for the treatment, amelioration or prevention of bone marrow cell death.

57. The method of claim 46, wherein said compound is administered as part of a pharmaceutical composition comprising a pharmaceutically acceptable carrier.

58. The method of claim 46, wherein said compound is administered after chemotherapy or radiation therapy of cancer in said animal.

59. The method of claim 46, wherein said compound is administered during chemotherapy or radiation therapy of cancer in said animal.

60. The method of claim 46, wherein said compound is administered prior to chemotherapy or radiation therapy of cancer in said animal.

61. The compound of claim 1, wherein $R_6$ and $R_7$ independently are hydrogen, alkyl, optionally substituted alkyl, $C_4$–$C_7$ cycloalkyl, heterocyclic, aryl or heteroaryl.

62. The compound of claim 1, wherein $R_6$ and $R_7$ are combined together with the nitrogen to form a heterocycle.

63. A compound having the Formula I:

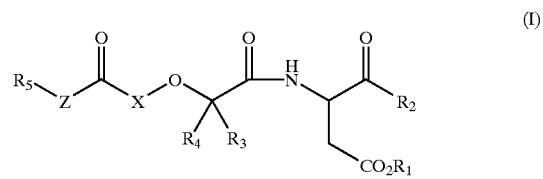

(I)

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond;

with the provisos that:

when Z is O, S or $(CR_9C_{10})_n$, then (a) when X is valine, and one of $R_3$ and $R_4$ is methyl, then $R_2$ is not arylacyloxyalkyl or acyloxyalkyl; and (b) when X is a bond, Z is $(CR_9R_{10})$, n is 0, and $R_3$ and $R_4$ are each hydrogen, then $R_2$ is not arylacyloxyalkyl or acyloxyalkyl.

64. The compound of claim 63, wherein Z is O.

65. The compound of claim 63, wherein Z is S.

66. The compound of claim 63, wherein Z is $NR_8$.

67. The compound of claim 63, wherein Z is $C(R_9R_{10})_n$.

68. The compound of claim 63, wherein $R_3$ and $R_4$ independently are hydrogen, aryl, heterocyclic, heteroaryl, $C_{1-10}$alkyl, alkenyl, alkynyl, or $C_{1-10}$alkyl substituted by one or more hydroxy, halogen, carboxy, amino, amide, ester, guanadino, thiol, alkylthiol, aryl, heterocyclic, or heteroaryl groups; and $R_5$ is an optionally substituted alkyl, $C_4$–$C_7$ cycloalkyl, saturated or unsaturated heterocyclic, aryl or heteroaryl group.

69. A compound according to claim 63, wherein $R_1$ is H, Me, Et or acetoxymethyl.

70. A compound according to claim 63, wherein $R_2$ is hydrogen, fluoromethyl, acyloxymethyl, arylacyloxymethyl, aryloxymethyl, heteroaryloxymethyl, or aminomethyl.

71. A compound according to claim 63, wherein X is a bond.

72. A compound according to claim 63, wherein Z is O, S, NH or $CH_2$.

73. A compound according to claim 63, wherein $R_3$ is hydrogen and $R_4$ is straight-chained or branched $C_{1-6}$ alkyl, cycloalkyl, aryl or heteroaryl.

74. A compound according to claim 63, wherein $R_3$ is hydrogen and $R_5$ is straight-chained or branched $C_{1-6}$ alkyl optionally substituted by hydroxy, halogen, carboxy, amino, amide, ester, guanadino, thiol, alkylthiol, aryl, heterocyclic or heteroaryl.

75. A compound according to claim 63, wherein $R_5$ is optionally substituted benzyl.

76. A compound according to claim 63, wherein $R_5$ is optionally substituted phenyl, naphthyl or heteroaryl.

77. A compound according to claim 63, wherein X a peptide of 1–2 amino acids.

78. A pharmaceutical composition, comprising a compound of claim 63, and a pharmaceutically acceptable carrier.

79. A method of inhibiting cell death of a cell or tissue, comprising contacting said cell or tissue with an effective amount of a compound of claim 63.

80. A method of treating or ameliorating cell death in the central or peripheral nervous system, retinal neurons, cardiac muscle or immune system cells of an animal, comprising administering to the animal in need of such treatment or ameliorating an effective amount of a compound of claim 63.

81. The method of claim 80, wherein said cell death is in the central or peripheral nervous system, and is due to one of:

(a) a condition of ischemia and excitotoxicity selected from the group consisting of focal ischemia due to stroke and global ischemia due to cardiac arrest;

(b) traumatic injury;

(c) viral infection;

(d) radiation-induced nerve cell death;

(e) a neurodegenerative disorder selected from the group consisting of Alzheimer's disease, Parkinson's Disease, a prion disease, multiple sclerosis, amyotrophic lateral sclerosis, and spinobulbar atrophy;

(f) spinal cord injury; or (g) acute bacterial meningitis.

82. The method of claim 80, wherein said cell death is in the central or peripheral nervous system, and is due to expansion of trinucleotide repeats of the Huntington's Disease gene.

83. The method of claim 80, wherein said cell death is due to Huntington's Disease.

84. The method of claim 80, wherein said cell death is in cardiac muscle tissue, and is due to myocardial infarction, congestive heart failure, cardiomyopathy or viral infection of the heart.

85. The method of claim 80, wherein said cell death is in retinal neurons and is due to increased intraocular pressure, age-related macular degeneration or retinitis pigmentosa.

86. The method of claim 80, wherein said cell death is in the immune system, and is due to an immune deficiency disorder selected from the group consisting of acquired immune deficiency syndrome, severe combined immune deficiency syndrome and radiation-induced immune suppression.

87. The method of claim 80, wherein said cell death is due to an autoimmune disorder selected from the group consisting of lupus erythematosus, rheumatoid arthritis and type I diabetes.

88. The method of claim 80, wherein said cell death is due to type I diabetes.

89. A method of treating or preventing polycystic kidney disease, renal amyloidosis, acute renal failure, cyclosporine A induced murin tubular epithelial cell death, HIV-induced nephropathy or anemia/erythropoiesis in an animal, comprising administering to the animal in need of such treatment or preventing an effective amount of a compound of claim 63.

90. A method of protecting a mammalian organ or tissue from cell death due to deprivation of normal blood supply, comprising contacting said organ or tissue with an effective amount of a compound of claim 63.

91. The method of claim 90, wherein said organ or tissue is present in a storage medium prior to transplant into a mammal.

92. The method of claim 90, wherein said tissue is embryonic nigral tissue.

93. The method of claim 90, wherein said contacting comprises infusion of said compound into the organ or tissue, or bathing of said organ or tissue in a storage medium which comprises said compound.

94. A method of reducing or preventing cell death in a donor organ or tissue after it has been transplanted into a host due to the effects of host immune cells, comprising administering to said host in need thereof an effective amount of a compound of claim 63.

95. A method of reducing or preventing the death of mammalian sperm or eggs used in in vitro fertilization procedures, comprising contacting said sperm or egg with an effective amount of a compound of claim 63.

96. A method of extending the lifespan of a mammalian or yeast cell line, comprising contacting said cell line with a compound of claim 63.

97. The method of claim 96, wherein said contacting comprises including said compound in a cell growth medium.

98. A method of treating or ameliorating hair loss or premature graying of the hair in a mammal, comprising contacting the hair or hair follicles of the mammal in need thereof with a compound of claim 63.

99. The method of claim 98, wherein hair loss is treated, and said hair loss is due to male-pattern baldness, radiation, chemotherapy or emotional stress.

100. A method of treating or ameliorating skin damage of a mammal due to exposure to high levels of radiation, heat or chemicals, comprising applying to the skin of the mammal in need thereof with a compound of claim 63.

101. The method of claim 100, wherein said compound is applied as part of an ointment.

102. The method of claim 100, wherein said skin damage is due to acute over-exposure to the sun, and wherein said treating reduces blistering and peeling of the skin.

103. A method of treating or ameliorating sepsis in an animal, comprising administering to the animal in need thereof an effective amount of a compound of claim 63.

104. A method of treating or ameliorating hepatitis in an animal, comprising administering to the animal in need thereof an effective amount of a compound of claim 63.

105. A method of treating or ameliorating hereditary tyrosinemia type 1 in an animal, comprising administering to the animal in need thereof an effective amount of a compound of claim 63.

106. A method of treating or ameliorating chronic alcohol ingestion induced buccal mucosa cell death in an animal, comprising administering to the animal in need thereof an effective amount of a compound of claim 63.

107. A method of treating or ameliorating cell death in plants or flowers, comprising administering to the plants or flowers in need thereof an effective amount of a compound of claim 63.

108. A method of treating or ameliorating radiation or ultraviolet-irradiation induced cell death in an animal, comprising administering to the animal in need thereof an effective amount of a compound of claim 63.

109. A method of treating or ameliorating apoptotic death of bone marrow cells in myelodysplastic syndromes (MDS), in an animal comprising administering to the animal in need thereof an effective amount of a compound of claim 63.

110. A method of treating or ameliorating apoptotic cell death in acute pancreatitis, in an animal comprising administering to the animal in need thereof an effective amount of a compound of claim 63.

111. A method of treating or ameliorating the inflammatory response in psoriasis or inflammatory bowel disease, in an animal comprising administering to the animal in need thereof an effective amount of a compound of claim 63.

112. A method of treating or ameliorating organ apoptosis after burn injury, in an animal comprising administering to the animal in need thereof an effective amount of a compound of claim 63.

113. A method of treating or ameliorating small bowel tissue injury after intestinal ischemia-reperfusion, in an animal comprising administering to the animal in need thereof an effective amount of a compound of claim 63.

114. A method of treating, ameliorating or preventing oral mucositis, gastrointestinal mucositis, bladder mucositis, proctitis, bone marrow cell death, skin cell death or hair loss resulting from chemotherapy or radiation therapy of cancer in an animal, comprising administering to the animal in need thereof an effective amount of a compound of claim 63.

115. The method of claim 114, wherein said compound is administered topically or orally.

116. The method of claim 115, wherein said compound is formulated as part of a mouthwash for the treatment, amelioration or prevention of oral mucositis.

117. The method of claim 115, wherein said compound is formulated as part of a slow release buccal lozenge.

118. The method of claim 115, wherein said compound is formulated as part of a suppository.

119. The method of claim 115, wherein said compound is formulated as part of a gel.

120. The method of claim 115, wherein said compound is administered through a bladder catheter for the treatment, amelioration or prevention of bladder mucositis.

121. The method of claim 115, wherein said compound is administered as part of an enema for the treatment, amelioration or prevention of proctitis.

122. The method of claim 115, wherein said compound is formulated as an oral formulation which is capable of coating the gastrointestinal surfaces for the treatment, amelioration or prevention of gastrointestinal mucositis.

123. The method of claim 122, wherein said gastrointestinal mucositis is esophageal mucositis, gastric mucositis, or intestinal mucositis.

124. The method of claim 115, wherein said compound is administered by i.v. injection for the treatment, amelioration or prevention of bone marrow cell death.

125. The method of claim 115, wherein said compound is administered as part of a pharmaceutical composition comprising a pharmaceutically acceptable carrier.

126. The method of claim 115, wherein said compound is administered after chemotherapy or radiation therapy of cancer in said animal.

127. The method of claim 115, wherein said compound is administered during chemotherapy or radiation therapy of cancer in said animal.

128. The method of claim 115, wherein said compound is administered prior to chemotherapy or radiation therapy of cancer in said animal.

129. A method of treating or ameliorating cell death in the central or peripheral nervous system, retinal neurons, cardiac muscle or immune system cells of an animal, comprising administering to the animal in need of such treatment or ameliorating an effective amount of a compound having the Formula I:

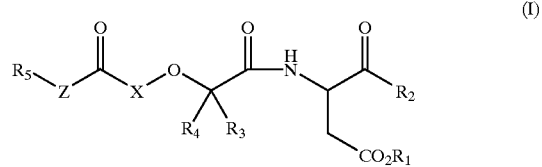

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond;

wherein said cell death is:
(a) in the central or peripheral nervous system, and is due to expansion of trinucleotide repeats of the Huntington's Disease gene;
(b) due to Huntington's Disease;
(c) in cardiac muscle tissue, and is due to myocardial infarction, congestive heart failure, cardiomyopathy or viral infection of the heart;
(d) in retinal neurons and is due to increased intraocular pressure, age-related macular degeneration or retinitis pigmentosa; or (e) in the immune system, and is due to an immune deficiency disorder selected from the group consisting of acquired immune deficiency syndrome, severe combined immune deficiency syndrome and radiation-induced immune suppression.

130. The method of claim 129, wherein said cell death is in the central or peripheral nervous system, and is due to expansion of trinucleotide repeats of the Huntington's Disease gene.

131. The method of claim 129, wherein said cell death is due to Huntington's Disease.

132. The method of claim 129, wherein said cell death is in cardiac muscle tissue, and is due to myocardial infarction, congestive heart failure, cardiomyopathy or viral infection of the heart.

133. The method of claim 129, wherein said cell death is in retinal neurons and is due to increased intraocular pressure, age-related macular degeneration or retinitis pigmentosa.

134. The method of claim 129, wherein said cell death is in the immune system, and is due to an immune deficiency disorder selected from the group consisting of acquired immune deficiency syndrome, severe combined immune deficiency syndrome and radiation-induced immune suppression.

135. A method of protecting a mammalian organ or tissue from cell death due to deprivation of normal blood supply, comprising contacting said organ or tissue with an effective amount of a compound having the Formula I:

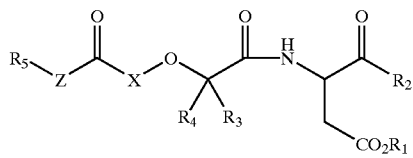

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond.

136. The method of claim 135, wherein said organ or tissue is present in a storage medium prior to transplant into a mammal.

137. The method of claim 135, wherein said tissue is embryonic nigral tissue.

138. The method of claim 135, wherein said contacting comprises infusion of said compound into the organ or tissue, or bathing of said organ or tissue in a storage medium which comprises said compound.

139. A method of reducing or preventing cell death in a donor organ or tissue after it has been transplanted into a host due to the effects of host immune cells, comprising administering to said host in need thereof an effective amount of a compound having the Formula I:

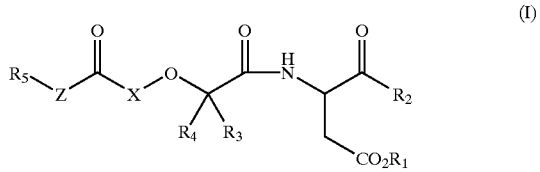

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond.

140. A method of reducing or preventing the death of mammalian sperm or eggs used in in vitro fertilization procedures, comprising contacting said sperm or egg with an effective amount of a compound having the Formula I:

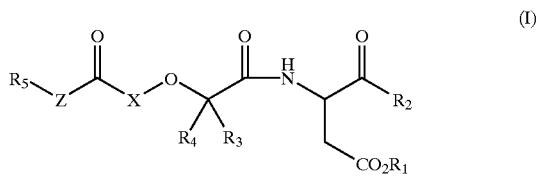

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond.

141. A method of extending the lifespan of a mammalian or yeast cell line, comprising contacting said cell line with a compound having the Formula I:

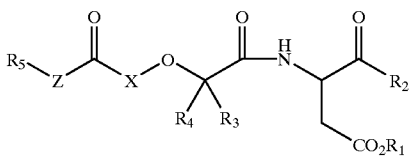

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond.

142. The method of claim 141, wherein said contacting comprises including said compound in a cell growth medium.

143. A method of treating or ameliorating hair loss or premature graying of the hair in a mammal, comprising contacting the hair or hair follicles of the mammal in need thereof with a compound having the Formula I:

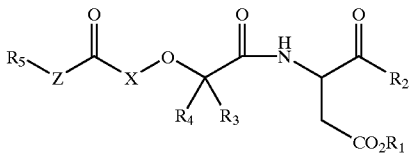

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond.

144. The method of claim 143, wherein hair loss is treated, and said hair loss is due to male-pattern baldness, radiation, chemotherapy or emotional stress.

145. A method of treating or ameliorating skin damage of a mammal due to exposure to high levels of radiation, heat or chemicals, comprising applying to the skin of the mammal in need thereof with a compound having the Formula I:

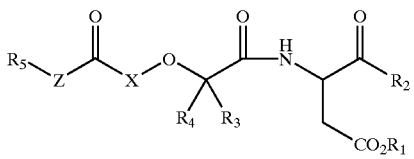

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond.

146. The method of claim 145, wherein said compound is applied as part of an ointment.

147. The method of claim 145, wherein said skin damage is due to acute over-exposure to the sun, and wherein said treating reduces blistering and peeling of the skin.

148. A method of treating a condition in an animal, wherein said condition is selected from the group consisting of:
(a) hereditary tyrosinemia type 1;
(b) chronic alcohol injestion induced buccal mucosa cell death;
(c) radiation or ultraviolet-radiation induced cell death;
(d) apoptotic cell death of bone marrow cells in myelodysplastic syndromes (MDS);
(e) organ apoptosis after burn injury; and
(f) small bowel tissue injury after intestinal ischemia-reperfusion;

comprising administering to the animal in need thereof an effective amount of a compound an effective amount of a compound having the Formula I:

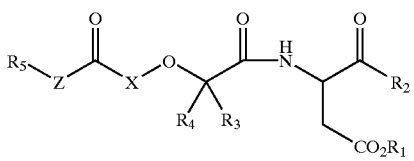

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond.

149. The method of claim 148, wherein said condition is hereditary tyrosinemia type 1.

150. The method of claim 148, wherein said condition is chronic alcohol ingestion induced buccal mucosa cell death.

151. The method of claim 148, wherein said condition is radiation or ultraviolet-radiation induced cell death.

152. The method of claim 148, wherein said condition is apoptotic cell death of bone marrow cells in myelodysplastic syndromes (MDS).

153. The method of claim 148, wherein said condition is organ apoptosis after burn injury.

154. The method of claim 148, wherein said condition is small bowel tissue injury after intestinal ischemia-reperfusion.

155. A method of treating or ameliorating cell death in plants or flowers, comprising administering to the plants or flowers in need thereof an effective amount of a compound having the Formula I:

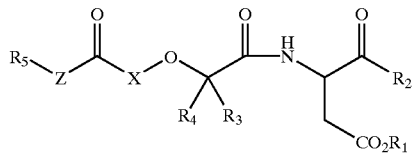

(I)

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond.

156. A method of treating, ameliorating or preventing oral mucositis, gastrointestinal mucositis, bladder mucositis, proctitis, bone marrow cell death, skin cell death or hair loss resulting from chemotherapy or radiation therapy of cancer in an animal, comprising administering to the animal in need thereof an effective amount of a compound having the Formula I:

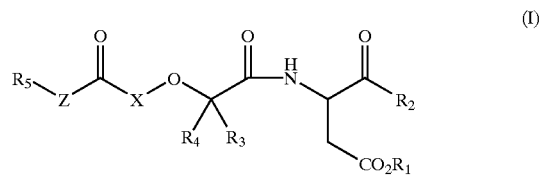

(I)

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1–2 amino acids or a bond.

157. The method of claim 150, wherein said compound is administered topically or orally.

158. The method of claim 157, wherein said compound is formulated as part of a mouthwash for the treatment, amelioration or prevention of oral mucositis.

159. The method of claim 157, wherein said compound is formulated as part of a slow release buccal lozenge.

160. The method of claim 157, wherein said compound is formulated as part of a suppository.

161. The method of claim 157, wherein said compound is formulated as part of a gel.

162. The method of claim 156, wherein said compound is administered through a bladder catheter for the treatment, amelioration or prevention of bladder mucositis.

163. The method of claim 156, wherein said compound is administered as part of an enema for the treatment, amelioration or prevention of proctitis.

164. The method of claim 156, wherein said compound is formulated as an oral formulation which is capable of coating the gastrointestinal surfaces for the treatment, amelioration or prevention of gastrointestinal mucositis.

165. The method of claim 164, wherein said gastrointestinal mucositis is esophageal mucositis, gastric mucositis, or intestinal mucositis.

166. The method of claim 156, wherein said compound is administered by i.v. injection for the treatment, amelioration or prevention of bone marrow cell death.

167. The method of claim 156, wherein said compound is administered as part of a pharmaceutical composition comprising a pharmaceutically acceptable carrier.

168. The method of claim 156, wherein said compound is administered after chemotherapy or radiation therapy of cancer in said animal.

169. The method of claim 156, wherein said compound is administered during chemotherapy or radiation therapy of cancer in said animal.

170. The method of claim 156, wherein said compound is administered prior to chemotherapy or radiation therapy of cancer in said animal.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Homo sapiens

<400> SEQUENCE: 1

Asp Glu Val Asp
1

<210> SEQ ID NO 2
<211> LENGTH: 5
<212> TYPE: PRT
<213> ORGANISM: Artificial
<220> FEATURE:
<213> OTHER INFORMATION: peptide ICE inhibitor fragment

<400> SEQUENCE: 2

Ala Tyr Val His Asp
1               5